United States Patent [19]
Brewer et al.

[11] Patent Number: 5,899,924
[45] Date of Patent: May 4, 1999

[54] SINGLE CAPACITOR TRUNCATED DAMPED SINUSOIDAL DEFIBRILLATION WAVEFORM

[75] Inventors: James E. Brewer, Cottage Grove; Gary B. Stendahl, Crystal, both of Minn.

[73] Assignee: SurVivaLink Corporation, Minneapolis, Minn.

[21] Appl. No.: 08/833,935

[22] Filed: Apr. 10, 1997

Related U.S. Application Data

[60] Provisional application No. 60/015,343, Apr. 12, 1996.

[51] Int. Cl.⁶ ................................................. A61N 1/39
[52] U.S. Cl. ....................................... 607/5; 607/7
[58] Field of Search ................................. 607/5, 7

[56] References Cited

U.S. PATENT DOCUMENTS

| | | | |
|---|---|---|---|
| 4,165,749 | 8/1979 | Cansell | 607/5 |
| 4,619,265 | 10/1986 | Morgan et al. | 607/7 |
| 4,768,512 | 9/1988 | Imran . | |
| 5,342,400 | 8/1994 | Hirschberg et al. . | |
| 5,391,186 | 2/1995 | Kroll et al. . | |
| 5,431,686 | 7/1995 | Kroll et al. . | |
| 5,468,254 | 11/1995 | Hahn et al. . | |
| 5,534,015 | 7/1996 | Kroll et al. | 607/5 |
| 5,540,723 | 7/1996 | Ideker et al. | 607/7 |
| 5,593,427 | 1/1997 | Gilner et al. | 607/7 |
| 5,601,612 | 2/1997 | Gilner et al. . | |
| 5,607,454 | 3/1997 | Cameron et al. | 607/5 |

FOREIGN PATENT DOCUMENTS

| | | |
|---|---|---|
| WO 95/09673 | 4/1995 | European Pat. Off. . |
| WO 95/32020 | 11/1995 | European Pat. Off. . |
| 9316759 | 9/1993 | WIPO ........................................ 607/5 |

OTHER PUBLICATIONS

The Journal of General Physiology, Rockefeller Institute for Medical Research, vol. 15, pp. 731–755, 1932.
Pacing and Clinical Electrophysiology, Futura Publishing Co., vol. 18, No. 4, pp. 633–758, Apr. 1995.
Journal of Cardiovascular Electrophysiology, Futura Publishing Co., vol.6, No. 9, Sep. 1995.
Pacing and Clinical Electrophysiology, Futura Publishing Co., vol. 18, No. 3, Part II, pp. 505–631, Mar. 1995.
Pacing and Clinical Electrophysiology, Futura Publishing Co., vol. 19, No. 8, pp. 1141–1272, Aug. 1996.
Pacing and Clinical Electrophysiology, Futura Publishing Co., vol. 17, No. 11, Part I, pp. 1707–1836, Nov. 1994.
The Journal of General Physiology, Rockefeller Institute for Medical Research, vol. 15, pp. 708–729, 1932.
Journal of the American College of Cardiology, American College of Cardiology, vol. 13, No. 1, Jan. 1989.
Pacing and Clinical Electrophysiology, Futura Publishing Co., vol. 16, No. 4, Part I, pp. 693–827, Apr. 1993.

(List continued on next page.)

*Primary Examiner*—William E. Kamm
*Assistant Examiner*—Carl H. Layno
*Attorney, Agent, or Firm*—Patterson & Keough, P.A.

[57] ABSTRACT

A method and apparatus for delivering a truncated damped sinusoidal external defibrillation waveform which, when applied through a plurality of electrodes positioned on a patient's torso will produce a desired response in the patient's cardiac cell membranes is provided. The method includes the steps monitoring a patient-dependent electrical parameter and determining a duration based on the parameter determined. A first set of charge storage capacitors is then charged. A first truncating switch is then closed to discharge the first set of capacitors. Then, after the duration period that was calculated has expired the switch is opened to truncate the waveform. The computation of discharge duration is made as a function of the desired cardiac membrane response function, a patient model and a defibrillator circuit model.

52 Claims, 9 Drawing Sheets

OTHER PUBLICATIONS

Circulation, American Heart Association, vol. 82, No. 6, pp. 2128–2141, Dec. 1990.

Circulation, American Heart Association, vol. 76, No. 5, pp. 1176–1184, Nov. 1987.

Circulation, American Heart Association, vol. 91, No. 6, pp. 1768–1774, Mar. 1995.

Circulation, American Heart Association, vol. 92, No. 6, pp. 1634–1643, Sep. 1995.

Circulation, American Heart Associate, vol. 94, No. 10, pp. 2507–2514, Nov. 1996.

SINGLE CAPACITOR TRUNCATED DAMPED SINUSOIDAL DEFIBRILLATION WAVEFORM

RELATED APPLICATIONS

This application is based on provisional patent application Ser. No: 60/015,343, filed Apr. 12, 1996 entitled METHOD OF DESIGNING EXTERNAL DEFIBRILLATOR WAVEFORMS, the contents of which are herein incorporated by reference and priority back to the Apr. 12, 1996 filing date is hereby claimed.

FIELD OF THE INVENTION

This invention relates generally to an electrotherapy method and apparatus for delivering an electrical pulse to a patient's heart. In particular, this invention relates to a method and apparatus for creating a truncated damped sinusoidal electrical waveform delivered by an external defibrillator based on theory and practice as described herein.

BACKGROUND OF THE INVENTION

Devices for defibrillating a heart have been known for sometime now. Implantable defibrillators are well accepted by the medical community as effective tools to combat fibrillation for an identified segment of the population. A substantial amount of research in fibrillation and the therapy of defibrillation has been done. Much of the most recent research has concentrated on understanding the effects that a defibrillation shock pulse has on fibrillation to terminate such a condition.

A monophasic waveform is defined to be a single phase, capacitive-discharge, time-truncated, waveform with exponential decay. A biphasic waveform is defined to comprise two monophasic waveforms, separated by time and of opposite polarity. The first phase is designated $\phi_1$ and the second phase is designated $\phi_2$. The delivery of $\phi_1$ is completed before the delivery of $\phi_2$ is begun.

After extensive testing, it has been determined that biphasic waveforms are more efficacious than monophasic waveforms. There is a wide debate regarding the reasons for the increased efficacy of biphasic waveforms over that of a monophasic waveforms. One hypothesis holds that $\phi_1$ defibrillates the heart and $\phi_2$ performs a stabilizing action that keeps the heart from refibrillating.

Biphasic defibrillation waveforms are now the standard of care in clinical use for defibrillation with implantable cardioverter-defibrillators (ICDs), due to the superior performance demonstrated over that of comparable monophasic waveforms. To better understand these significantly different outcomes, ICD research has developed cardiac cell response models to defibrillation. Waveform design criteria have been derived from these first principles and have been applied to monophasic and biphasic waveforms to optimize their parameters. These principles-based design criteria have produced significant improvements over the current art of waveforms.

In a two paper set, Blair developed a model for the optimal design of a monophasic waveform when used for electrical stimulation. (1) Blair, H. A., "On the Intensity-time relations for stimulation by electric currents." I. J. Gen. Physiol. 1932; 15:709–729. (2) Blair, H. A., "On the Intensity-time Relations for stimulation by electric currents". II. J. Gen. Physiol. 1932; 15:731–755. Blair proposed and demonstrated that the optimal duration of a monophasic waveform is equal to the point in time at which the cell response to the stimulus is maximal. Duplicating Blair's model, Walcott extended Blair's analysis to defibrillation, where they obtained supporting experimental results. Walcott, et al., "Choosing the optimal monophasic and biphasic waveforms for ventricular defibrillation." J. Cardiovasc Electrophysiol. 1995; 6:737–750.

Independently, Kroll developed a biphasic model for the optimal design of $\phi_2$ for a biphasic defibrillation waveform. Kroll, M. W., "A minimal model of the single capacitor biphasic defibrillation waveform." PACE 1994; 17:1782–1792. Kroll proposed that the $\phi_2$ stabilizing action removed the charge deposited by $\phi_1$ from those cells not stimulated by $\phi_1$. This has come to be known as "charge burping". Kroll supported his hypothesis with retrospective analysis of studies by Dixon, et al., Tang, et al., and Freese, et al. regarding single capacitor, biphasic waveform studies. Dixon, et al., "Improved defibrillation thresholds with large contoured epicardial electrodes and biphasic waveforms." Circulation 1987; 76:1176–1184; Tang, et al. "Ventricular defibrillation using biphasic waveforms: The Importance of Phasic duration." J. Am. Coll. Cardiol. 1989; 13:207–214; and Feeser, S. A., et al. "Strength-duration and probability of success curves for defibrillation with biphasic waveforms." Circulation 1990; 82:2128–2141. Again, the Walcott group retrospectively evaluated their extension of Blair's model to $\phi_2$ using the Tang and Feeser data sets. Their finding further supported Kroll's hypothesis regarding biphasic defibrillation waveforms. For further discussions on the development of these models, reference may be made to PCT publications WO 95/32020 and WO 95/09673 and to U.S. Pat. No. 5,431,686.

The charge burping hypothesis can be used to develop equations that describe the time course of a cell's membrane potential during a biphasic shock pulse. At the end of $\phi_1$, those cells that were not stimulated by $\phi_1$ have a residual charge due to the action of $\phi_1$ on the cell. The charge burping model hypothesizes that an optimal pulse duration for $\phi_2$ is that duration that removes as much of the $\phi_1$ residual charge from the cell as possible. Ideally, these unstimulated cells are set back to "relative ground." The charge burping model proposed by Kroll is based on the circuit model shown in FIG. 2b which is adapted from the general model of a defibrillator illustrated in FIG. 2a.

The charge burping model also accounts for removing the residual cell membrane potential at the end of a $\phi_1$ pulse that is independent of a $\phi_2$. That is, $\phi_2$ is delivered by a set of capacitors separate from the set of capacitors used to deliver $\phi_1$. This charge burping model is constructed by adding a second set of capacitors, as illustrated in FIG. 3. In this figure, $C_1$ represents the $\phi_1$ capacitor set, $C_2$ represents the $\phi_2$ capacitor set $R_H$ represents the resistance of the heart, and the pair $C_M$ and $R_M$ represent membrane series capacitance and resistance of a single cell. The node $V_S$ represents the voltage between the electrodes, while $V_M$ denotes the voltage across the cell membrane.

External defibrillators send electrical pulses to the patient's heart through electrodes applied to the patient's torso. External defibrillators are useful in any situation where there may be an unanticipated need to provide electrotherapy to a patient on short notice. The advantage of external defibrillators is that they may be used on a patient as needed, then subsequently moved to be used with another patient.

However, this important advantage has two fundamental limitations. First, external defibrillators do not have direct contact with the patient's heart. External defibrillators have traditionally delivered their electrotherapeutic pulses to the patient's heart from the surface of the patient's chest. This is known as the transthoracic defibrillation problem. Second, external defibrillators must be able to be used on patients having a variety of physiological differences. External defibrillators have traditionally operated according to pulse amplitude and duration parameters that can be effective in all patients. This is known as the patient variability problem.

The prior art described above effectively models implantable defibrillators, however it does not fully addressed the transthoracic defibrillation problem nor the patient variability problem. In fact, these two limitations to external defibrillators are not fully appreciated by those in the art. For example, prior art disclosures of the use of truncated monophasic or biphasic shock pulses in implantable or external defibrillators have provided little guidance for the design of an external defibrillator that will successfully defibrillate across a large, heterogeneous population of patients. In particular, an implantable defibrillator and an external defibrillator can deliver a shock pulse of similar form, and yet the actual implementation of the waveform delivery system is radically different.

In the past five years, new research in ICD therapy has developed and demonstrated defibrillation models that provide waveform design rules from first principles. These defibrillation models and their associated design rules for the development of defibrillation waveforms and their characteristics were first developed by Kroll and Irnich for monophasic waveforms using effective and rheobase current concepts. (1) Kroll, M. W., "A minimal model of the monophasic defibrillation pulse." PACE 1993; 15:769. (2) Irnich, W., "Optimal truncation of defibrillation pulses." PACE 1995; 18:673. Subsequently, Kroll, Walcott, Cleland and others developed the passive cardiac cell membrane response model for monophasic and biphasic waveforms, herein called the cell response model. (1) Kroll, M. W., "A minimal model of the single capacitor biphasic defibrillation waveform." PACE 1994; 17:1782. (2) Walcott, G.P., Walker, R. G., Cates. A. W., Krassowska, W., Smith, W. M, Ideker R E. "Choosing the optimal monophasic and biphasic waveforms for ventricular defibrillation." J Cardiovasc Electrophysiol 1995; 6:737; and Cleland B G. "A conceptual basis for defibrillation waveforms." PACE 1996; 19:1186).

A significant increase in the understanding of waveform design has occurred and substantial improvements have been made by using these newly developed design principles. Block et al. has recently written a comprehensive survey of the new principles-based theories and their impact on optimizing internal defibrillation through improved waveforms. Block M, Breithardt G., "Optimizing defibrillation through improved waveforms." PACE 1995; 18:526.

There have not been significant developments in external defibrillation waveforms beyond the two basic monophasic waveforms: the damped sine or the truncated exponential. To date, their design for transthoracic defibrillation has been based almost entirely on empirically derived data. It seems that the design of monophasic and biphasic waveforms for external defibrillation has not yet been generally influenced by the important developments in ICD research.

Recently there has been reported research on the development and validation of a biphasic truncated exponential waveform in which it was compared clinically to a damped sine waveform. For additional background, reference may be made to U.S. Pat. Nos. 5,593,427, 5,601,612 and 5,607,454. See also: Gliner B E, Lyster T E, Dillon S M, Bardy G H, "Transthoracic defibrillation of swine with monophasic and biphasic waveforms." Circulation 1995; 92:1634–1643; Bardy G H, Gliner B E, Kudenchuk P J, Poole J E, Dolack G L, Jones G K, Anderson J, Troutman C, Johnson G.; "Truncated biphasic pulses for transthoracic defibrillation." Circulation 1995; 91:1768–1774; and Bardy G H et al, "For the Transthoracic Investigators. Multicenter comparison of truncated biphasic shocks and standard damped sine wave monophasic shocks for transthoracic ventricular defibrillation." Circulation 1996; 94:2507–2514. Although the research determined a usable biphasic waveform, there was no new theoretical understanding determined for external waveform design. It appears that external waveform research may develop a "rules-of-thumb by trial and error" design approach much like that established in the early stages of theoretical ICD research. The noted limitations of the transthoracic biphasic waveform may be due in part to a lack of principles-based design rules to determine its waveform characteristics.

Monophasic defibrillation waveforms remain the standard of care in clinical use for transthoracic defibrillation. Waveform design has not yet been influenced by the important gains made in ICD research. The limitations of present transthoracic waveforms may be due in part to a lack of application of these design principles to determine optimal waveform characteristics. To overcome these limitations, design principles and design rules based on cell response have recently been developed for external defibrillation waveforms. The transthoracic model incorporates elements into a cell response model that extends it to external defibrillation.

Damped sine waves have been used and are well known to those skilled in the art of defibrillators for some time now. Known damped sine waveforms typically have a very large leading edge voltage which is damped by the inductor. Due to a rapid rise time, the known damped sine waveform implementations do not track the cell membrane response. By incorporating a larger inductor (25 mH–500 mH) and by truncating each phase of the delivery of the damped sine waveform at appropriate times defined by design rules based on a desired cardiac cell response, damped sine waveforms can better track cell membrane response, thereby providing a more effective defibrillation shock pulse.

There is a continued need for an apparatus and method for accurately delivering an external defibrillator waveform to efficiently and effectively provide a desired response in the patient cardiac cell membrane.

SUMMARY OF THE INVENTION

The present invention relates to an external defibrillation method and apparatus that addresses the limitations in the prior art. The present invention incorporates three singular practices that distinguish the practice of designing external defibrillators from the practice of designing implantable defibrillators. These practices are 1) designing multiphasic transthoracic shock pulse waveforms from principles based on cardiac electrophysiology, 2) designing multiphasic transthoracic shock pulse waveforms in which each phase of the waveform can be designed without implementation limitations placed on its charging and delivery means by such means for prior waveform phases, and 3) designing multiphasic transthoracic shock pulse waveforms to operate across a wide range of parameters determined by a large, heterogeneous population of patients.

In particular, the present invention provides for a method and apparatus for delivering a truncated damped sinusoidal external defibrillation waveform which, when applied through a plurality of electrodes positioned on a patient's torso, will produce a desired response in the patient's cardiac cell membrane. The method includes the steps of monitoring a patient-dependent electrical parameter and determining a duration based on the parameter determined. A first set of charge storage capacitors are then charged. A first truncating switch is then closed to discharge the first set of capacitors. Then, after the duration period that was calculated has expired the switch is opened to truncate the waveform. The computation of the discharge duration is made as a function of a desired cardiac membrane response function, a patient model and a defibrillator circuit model.

DESCRIPTION OF THE PREFERRED EMBODIMENT

The present invention provides a method and apparatus for delivering a truncated damped sinusoidal external defibrillation waveform which, when applied through a plurality of electrodes positioned on a patient's torso will provide a desired response in the patient's cardiac cell membrane. To better understand the present invention, a discussion of the development of an appropriate model is first needed.

Description of External Defibrillation Model

Figure 1A:
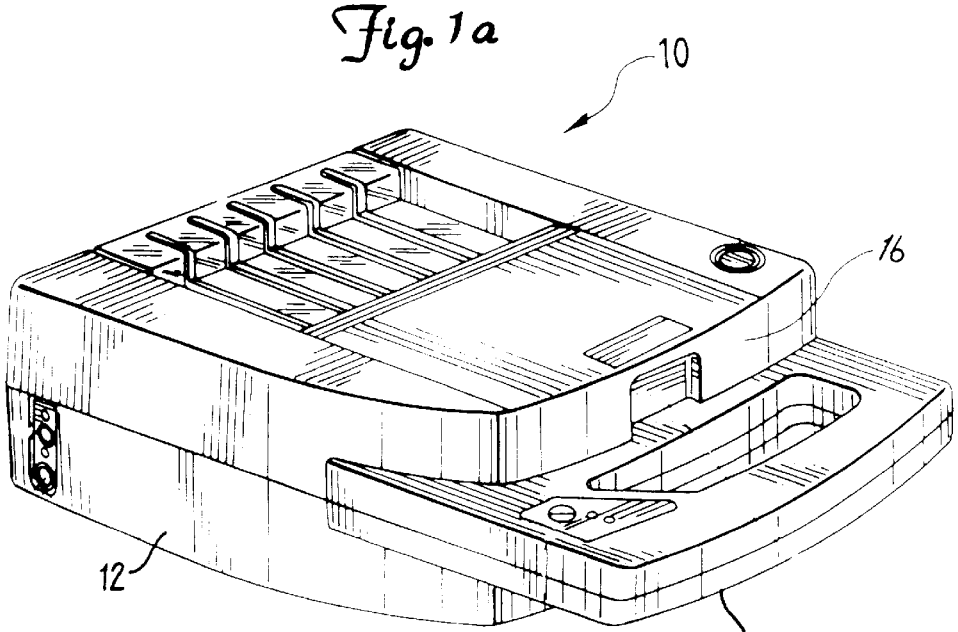
FIGS. 1a and 1b are perspective views of an AED according to the present invention.
Figure 1B:
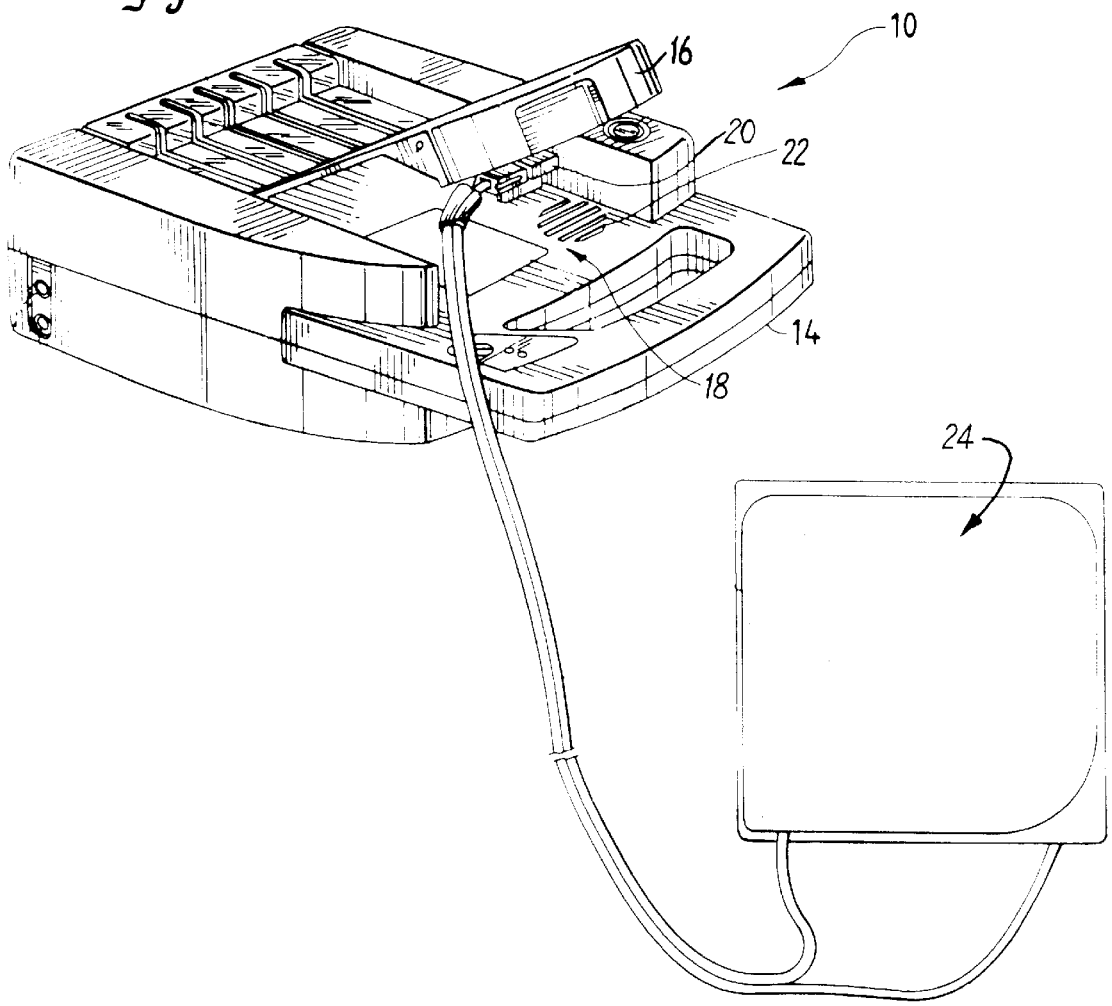

An automated external defibrillator (AED) is illustrated in FIGS. 1a and 1b. FIG. 1a illustrates an AED 10, including a plastic case 12 with a carrying handle 14. A lid 16 is provided which covers an electrode compartment 18. An electrode connector 20, a speaker 22 and a diagnostic panel (not shown) are located on case 12 within electrode compartment 18. FIG. 1b illustrates AED 10 having a pair of electrodes 24 connected thereto. Electrodes 24 can be pre-connected to connector 20 and stored in compartment 18.

The operation of AED 10 is described briefly below. A rescue mode of AED 10 is initiated when lid 16 is opened to access electrodes 24. The opening of lid 16 is detected by AED 10 to effectively turn on the device. AED 10 then quickly runs a short test routine. After electrodes 24 have been placed on the patient, AED 10 senses patient specific parameters, such as impedance, voltage, current, charge or other measurable parameters of the patient. The patient specific parameters are then utilized in the design of optimal waveforms as will be described below.

If a shockable condition is detected through electrodes 24, a plurality of capacitors inside of AED 10 are charged from an energy source, typically a detachable battery pack. Based upon the patient specific parameters sensed, the duration and other characteristics of a discharge waveform are then calculated. The energy stored in AED 10 is then discharged to the patient through electrodes 24.

For a more detailed description of the physical structure of AED 10 or the process involved in sensing, charging, shocking and testing, reference should be made to applicants co-pending application Ser. No. 08/512,441, filed Aug. 8, 1995 entitled AUTOMATED EXTERNAL DEFIBRILLATOR WITH SELF-TEST SYSTEM, which issued as U.S. Pat. No. 5,645,571 on Jul. 8, 1997, which is assigned to the assignee of the present invention, the disclosure of which is herein incorporated by reference.

It is not assumed that both phases of a biphasic waveform are delivered using the same set of capacitors or that both phases of a biphasic waveform are delivered using the capacitor set in the same electrical configuration, although such an embodiment is considered within the spirit and scope of the present invention.

Transthoracic defibrillation is generally performed by placing electrodes on the apex and anterior positions of the chest wall. With this electrode arrangement, nearly all current passing through the heart is conducted by the lungs and the equipotential surfaces pass through the myocardium normal to the electrode axis. The transthoracic charge burping model is used to develop design equations that describe the time course of a cell's membrane potential during a transthoracic biphasic shock pulse. These equations are then used to create equations that describe the design of monophasic and biphasic shock pulses for trans chest defibrillation to optimize the design of $\phi_1$ for defibrillating and the design of $\phi_2$ for stabilizing. These optimizing shock pulse design equations are called design rules.

The main series pathway for current is to pass through the chest wall, the lungs, and the heart. Additionally, there are two important shunting pathways in parallel with the current pathway through the heart. These shunting pathways must be taken into consideration. The lungs shunt current around the heart through a parallel pathway. The second shunting pathway is provided by the thoracic cage. The resistivity of the thoracic cage and the skeletal muscle structure is low when compared to lungs. The high resistivity of the lungs and the shunting pathways are characterizing elements of external defibrillation that distinguish the art from intracardiac defibrillation and implantable defibrillation technologies.

Figure 4:
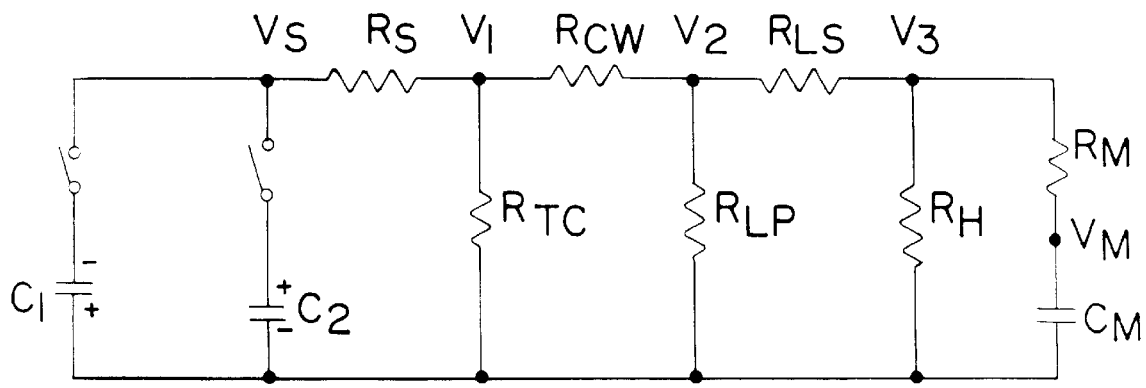
FIG. 4 represents a monophasic or biphasic capacitive-discharge external defibrillation model according to the present invention.

Therefore, in the transthoracic defibrillation model illustrated in FIG. 4, there are several resistances in addition to those discussed for the charge burping model above. $R_S$ represents the resistance of the defibrillation system, including the resistance of the defibrillation electrodes. $R_{CW}$ and $R_{LS}$ represent the resistances of the chest wall and the lungs, respectively, in series with resistance of the heart, $R_H$. $R_{TC}$ and $R_{LP}$ represent the resistances of the thoracic cage and the lungs, respectively, in parallel with the resistance of the heart.

The design rules for external defibrillation waveforms are determined in three steps. In the first step, the transchest forcing function is determined. The transchest forcing function is the name that is given to the voltage that is applied across each cardiac cell during an external defibrillation shock. In the second step, the design equations for $\phi_1$ of a shock pulse are determined. The design equations are the equations describing the cell's response to the $\phi_1$ transchest forcing function, the equation describing the optimal $\phi_1$ pulse duration, and the equation describing the optimal $\phi_1$ capacitor. Therefore, step two relates the cell response to the action of a monophasic shock pulse or the first phase of a biphasic shock pulse. This relation is used to determine the optimal design rules and thereby design parameters for the implementation of this phase in an external defibrillator. It will be clear to those in the art that step two is not restricted to capacitor discharge shock pulses and their associated transchest forcing function. Another common implementation of an external defibrillator incorporates a damped sine wave for a shock pulse and can be either a monophasic or biphasic waveform. This type of external defibrillator is modeled by the circuit shown in FIG. 5. In the third step, the design equations for $\phi_2$ of a shock pulse are determined. The design equations are the equations describing the cell's response to the $\phi_2$ transchest forcing function, the equation describing the optimal $\phi_2$ pulse duration and the equation describing the optimal $\phi_2$ capacitor. These design equations are employed to determine the optimal design rules and thereby design parameters of $\phi_2$ of a biphasic shock pulse with respect to how the cell responds to the shock pulse. An important element of this invention is to provide shock pulse waveforms that are designed from a cardiac cell response model developed from first principles and that correctly determines the effects of the chest and its components on the ability of a shock pulse to defibrillate.

The transchest forcing function is determined by solving for the voltage found at node $V_3$ in FIG. 4. The transchest forcing function is derived by solving for $V_3$ using the following three nodal equations:

$$\frac{V_1 - V_S}{R_S} + \frac{V_1}{R_{TC}} + \frac{V_1 - V_2}{R_{CW}} = 0, \quad (1)$$

$$\frac{V_2 - V_1}{R_{CW}} + \frac{V_2}{R_{LP}} + \frac{V_2 - V_3}{R_{LS}} = 0, \quad (2)$$

and $$\frac{V_3 - V_2}{R_{LS}} + \frac{V_3}{R_H} + \frac{V_3 - V_M}{R_M} = 0. \quad (3)$$

Equation 1 can be rewritten as $$V_1\left(\frac{1}{R_S} + \frac{1}{R_{TC}} + \frac{1}{R_{CW}}\right) = \frac{V_S}{R_S} + \frac{V_2}{R_{CW}}. \quad (4A)$$

$$V_1 = \frac{V_S}{R_S \Omega_1} + \frac{V_2}{R_{CW} \Omega_1}, \quad (4B)$$

where $$\Omega_1 = \frac{1}{R_S} + \frac{1}{R_{TC}} + \frac{1}{R_{CW}}.$$

Rewriting equation 2, we have $$V_2\left(\frac{1}{R_{CW}} + \frac{1}{R_{LP}} + \frac{1}{R_{LS}}\right) = \frac{V_1}{R_{CW}} + \frac{V_3}{R_{LS}}. \quad (4C)$$

By substituting equation 4B for $V_1$ into equation 4C, we can solve for $V_2$ as an expression of $V_S$ and $V_3$:

$$V_2 = \frac{V_S}{R_S R_{CW} \Omega_1 \Omega_2 \Omega_{22}} + \frac{V_3}{R_{LS} \Omega_2 \Omega_{22}}, \text{ where} \quad (5)$$

$$\Omega_2 = \frac{1}{R_{LS}} + \frac{1}{R_{LP}} + \frac{1}{R_{CW}}, \text{ and}$$

$$\Omega_{22} = 1 - \frac{1}{R_{CW}^2 \Omega_1 \Omega_2}.$$

Now solving for $V_3$ as an expression of $V_S$ and $V_M$, equation 3 may be re-arranged as $$V_3\left(\frac{1}{R_{LS}} + \frac{1}{R_H} + \frac{1}{R_M}\right) = \frac{V_2}{R_{LS}} + \frac{V_M}{R_M} \quad (6)$$

so that $$V_3 = \frac{V_2}{R_{LS}\Omega_3} + \frac{V_M}{R_M \Omega_3} \quad (7)$$

where $$\Omega_3 = \frac{1}{R_{LS}} + \frac{1}{R_H} + \frac{1}{R_M}.$$

Substituting equation 5 for $V_2$ into equation 7, we can solve for $V_3$ as an expression of $V_S$ and $V_M$:

$$V_3 = \frac{V_S}{R_S R_{CW} R_{LS} \Omega_1 \Omega_2 \Omega_{22} \Omega_3 \Omega_{33}} + \frac{V_M}{R_M \Omega_3 \Omega_{33}} \quad (8)$$

where $$\Omega_{33} = 1 - \frac{1}{(R_{LS}^2 \Omega_2 \Omega_{22} \Omega_3)} \quad (9)$$

From equation 8 we define $\Omega_M$ to be:

$$\Omega_M = R_M \Omega_3 \Omega_{33} = R_M \Omega_3\left(1 - \frac{1}{(R_{LS}^2 \Omega_2 \Omega_{22} \Omega_3)}\right) \quad (10)$$

$$\Omega_M = R_M\left(\Omega_3 - \frac{1}{R_{LS}^2\left(\Omega_2 - \frac{1}{R_{CW}^2 \Omega_1}\right)}\right).$$

Figure 5A:
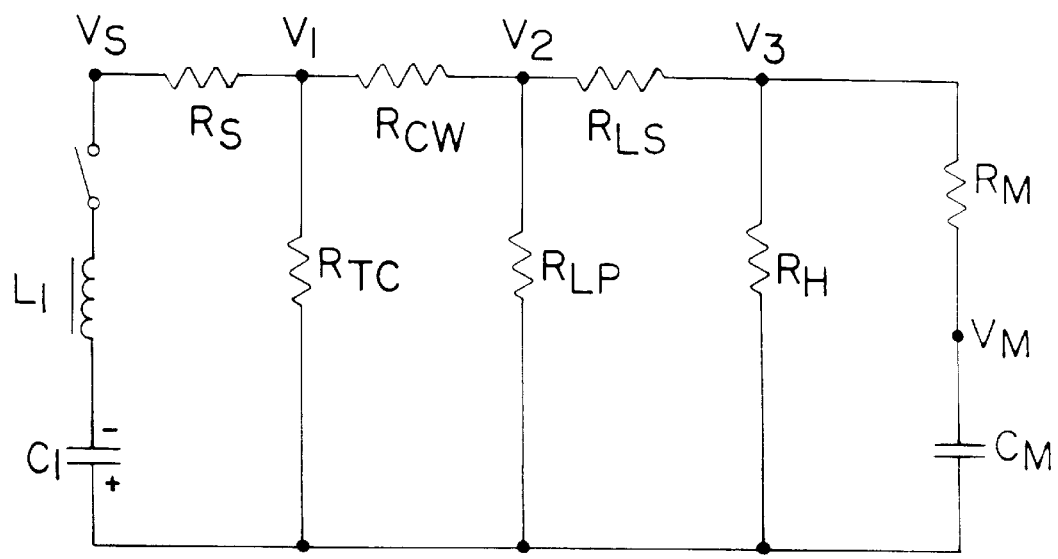
FIG. 5a represents a monophasic capacitor-inductor external defibrillator model according to the present invention.
Figure 5B:
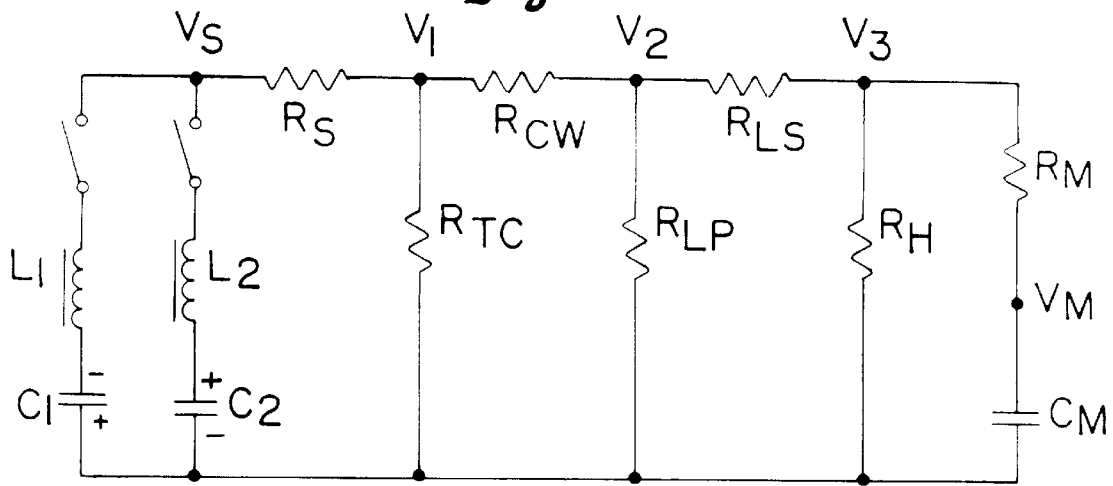
FIG. 5b represents an alternative embodiment of a biphasic capacitor-inductor external defibrillator model according to the present invention.

From equation 8 we also define $\Omega_S$ to be:

$$\Omega_S = R_S R_{CW} R_{LS} \Omega_1 \Omega_2 \Omega_3 \Omega_{22} \Omega_{33} \quad (11)$$

$$\Omega_S = R_S R_{CW} R_{LS} \Omega_1 \Omega_2\left(1 - \frac{1}{(R_{CW}^2 \Omega_1 \Omega_2)}\right)\Omega_3\left(1 - \frac{1}{(R_{LS}^2 \Omega_2 \Omega_{22} \Omega_3)}\right) \quad (12)$$

$$\Omega_S = R_S R_{CW} R_{LS}\left(\Omega_1 \Omega_2 - \frac{1}{R_{CW}^2}\right)\left(\Omega_3 - \frac{1}{R_{LS}^2\left(\Omega_2 - \frac{1}{R_{CW}^2 \Omega_1}\right)}\right) \quad (13)$$

so that $$V_3 = \frac{V_S}{\Omega_S} + \frac{V_M}{\Omega_M} \quad (14)$$

are the general transchest transfer function as shown in FIG. 4 or FIGS. 5a and 5b. Equation 14 incapsulates the transchest elements and their association between the forcing function $V_S$ (which models a defibrillation circuit and the shock pulse) and the cell membrane voltage $V_M$. Therefore, this completes the first step.

The variable $V_S$ may now be replaced with a more specific description of the defibrillation circuitry that implements a shock pulse. For a first example, a monophasic time-truncated, capacitive-discharge circuit may be represented by $V_S = V_1 e^{-t/\tau_1}$, where $V_1$ is the leading-edge voltage for the shock pulse and $\tau_1 = RC_1$, with R determined below.

As shown in FIGS. 5a and 5b, a second example would be a monophasic damped sine wave circuit, represented by $$V_S = V_1 \left(\frac{\tau_{C1}}{\tau_{C1} - \tau_{L1}}\right)(e^{-t/\tau_{C1}} - e^{-t/\tau_{L1}}) \quad (14B)$$

where $V_1$ is the voltage on the charged capacitor $C_1$, $\tau_{C1}=RC_1$ and $\tau_{L1}=L_1/R$. Every step illustrated below may be performed with this and other similar transchest forcing functions which represent defibrillator circuitry.

To proceed with step two, from FIG. 4, nodal analysis provides an equation for $V_M$:

$$C_M \frac{dV_M}{dt} + \frac{V_M - V_3}{R_M} = 0. \quad (15)$$

Rearranging equation 15, we have $$C_M \frac{dV_M}{dt} + \frac{V_M}{R_M} = \frac{V_3}{R_M}. \quad (16)$$

Next, substituting equation 14 as an expression for $V_3$ into equation 16, the cell membrane response is now calculated as follows:

$$C_M \frac{dV_M}{dt} + \frac{V_M}{R_M} = \frac{1}{R_M}\left(\frac{V_S}{\Omega_S} + \frac{V_M}{\Omega_M}\right) \quad (17)$$

$$C_M \frac{dV_M}{dt} + \frac{V_M}{R_M} - \frac{V_M}{R_M \Omega_M} = \frac{V_S}{R_M \Omega_S}$$

$$C_M \frac{dV_M}{dt} + \frac{V_M}{R_M}\left(1 - \frac{1}{\Omega_M}\right) = \frac{V_S}{R_M \Omega_S} \quad (18)$$

Dividing through by $C_M$, and setting $\tau_M = R_M C_M$, then equation 18 becomes $$\frac{dV_M}{dt} + \frac{V_M}{\tau_M}\left(1 - \frac{1}{\Omega_M}\right) = \frac{V_S}{\tau_M}\left(\frac{1}{\Omega_S}\right). \quad (19)$$

Equation 19 is a general ordinary differential equation (ODE) that models the effects of any general forcing function $V_S$ that represents a phase of a shock pulse waveform applied across the chest. The general ODE equation 19 models the effects of a general shock pulse phase $V_S$ on the myocardium, determining cardiac cell response to such a shock pulse phase.

In the equations given below:

$C_1$ equals the capacitance of the first capacitor bank and $V_S = V_1 e^{-t/\tau_1}$;

$C_2$ equals the capacitance of the second capacitor bank and $V_S = V_2 e^{-t/\tau_2}$;

$R = R_S + R_B$, where $R_S$=System impedance (device and electrodes);

$R_B$=body impedance (thoracic cage, chest wall, lungs (series, parallel), heart).

To determine body impedance, $R_B$, we see that the series combination of $R_H$ and $R_{LS}$ yields $R_H + R_{LS}$. (FIG. 4). The parallel combination of $R_H + R_{LS}$ and $R_{LP}$ yields:

$$\frac{R_{LP}(R_{LS} + R_H)}{R_{LP} + R_{LS} + R_H}. \quad (20)$$

The series combination of equation 20 and $R_{CW}$ yields:

$$R_{CW} + \frac{R_{LP}(R_{LS} + R_H)}{(R_{LP} + R_{LS} + R_H)}. \quad (21)$$

The parallel combination of equation 21 and $R_{TC}$ yields:

$$R_B = \left[\frac{R_{TC}\left[R_{CW} + \frac{R_{LP}(R_{LS} + R_H)}{(R_{LP} + R_{LS} + R_H)}\right]}{R_{TC} + R_{CW} + \frac{R_{LP}(R_{LS} + R_H)}{(R_{LP} + R_{LS} + R_H)}}\right] \quad (22)$$

where $R_B$ is the impedance of the body for this model.

The discharge of a single capacitor is modeled by $V_S = V_1 e^{-t/\tau_1}$ for an initial $C_1$ capacitor voltage of $V_1$. Placing $V_S$ into equation 19 gives:

$$\frac{dV_M}{dt} + \frac{V_M}{\tau_M}\left(1 - \frac{1}{\Omega_M}\right) = \frac{V_1 e^{-t/\tau_1}}{\tau_M \Omega_S} \quad (23)$$

where $\tau_M = R_M C_M$ represents the time constant of the myocardial cell in the circuit model, and $\tau_1$, which equals $R_S C_1$, represents the time constant of $\phi_1$. Such a standard linear ODE as equation 23 has the form $dy/dx + P(X)Y = Q(x)$. These linear ODEs have an integration factor that equals $e^{\int p dx}$. The general solution to such equations is:

$$Y = e^{-\int p dx}\left[\int e^{\int p dx} Q dx + c\right].$$

The ODE in equation 23 models the effects of each phase of a time-truncated, capacitor-discharged shock pulse waveform. Equation 23 is a first-order linear ODE, and may be solved using the method of integration factors, to get:

$$V_{M1}(t) = ke^{-(t/\tau_M)(1 - \frac{1}{\Omega_M})} + \left(\frac{V_1}{\Omega_S}\right)\left(\frac{\tau_1}{\tau_1\left(1 - \frac{1}{\Omega_M}\right) - \tau_M}\right)e^{-t/\tau_1}. \quad (24)$$

Equation 24 is an expression of cell membrane potential during $\phi_1$ of a shock pulse. To determine the constant of integration k, the initial value of $V_{M1}$ is assumed to be $V_{M1}(0) = V_G$ ("cell ground"). Applying this initial condition to equation 24, k is found to be $$k = V_G - \left(\frac{V_o}{\Omega_S}\right)\left(\frac{\tau_1}{\tau_1\left(1 - \frac{1}{\Omega_M}\right) - \tau_M}\right). \quad (25)$$

Assuming $\tau_1 = RC_1$, where $R = R_S + R_B$, then the solution to the initial-value problem for $\phi_1$ is:

$$V_{M1}(t) = V_G e^{-(t/\tau_M)(1 - \frac{1}{\Omega_M})} + \left(\frac{V_1}{\Omega_S}\right)\left(\frac{\tau_1}{\tau_1\left(1 - \frac{1}{\Omega_M}\right) - \tau_M}\right) \quad (26)$$

$$\left(e^{-t/\tau_1} - e^{-(t/\tau_M)(1 - \frac{1}{\Omega_M})}\right)$$

Equation 26 describes the residual voltage found on a cell at the end of $\phi_1$.

Assuming $V_G = 0$ and $V_1 = 1$, the solution for cell response to an external shock pulse is $$V_{M1}(t) = \left(\frac{1}{\Omega_S}\right)\left(\frac{1}{\tau_1\left(1 - \frac{1}{\Omega_M}\right) - \tau_M}\right)\left(e^{-\frac{t}{\tau_1}} - e^{-\left(\frac{t}{\tau_M}\right)\left(1 - \frac{1}{\Omega_M}\right)}\right). \quad (27)$$

We may now determine optimal durations for $\phi_1$ according to criteria for desired cell response. One such design role or criterion is that the $\phi_1$ duration is equal to the time required for the external defibrillator shock pulse to bring the cell response to its maximum possible level. To determine this duration, equation 27 is differentiated and the resulting equation 27B is set to zero. Equation 27B is then solved for the time t, which represents shock pulse duration required to maximize cardiac cell response.

$$\left(\frac{AB}{\tau_M}\right)e^{-Bt/\tau_M} - \left(\frac{A}{\tau_1}\right)e^{-t/\tau_1} = 0, \quad (27B)$$

where $$A = \left(\frac{1}{\Omega_S}\right)\left(\frac{\tau_1}{\tau_1\left(1 - \frac{1}{\Omega_M}\right) - \tau_M}\right)$$

and $$B = 1 - \frac{1}{\Omega_M}.$$

Solving for t, the optimal duration $d\phi_1$ for a monophasic shock pulse or $\phi_1$ of a biphasic shock pulse is found to be $$d\phi_1 = \left(\frac{\tau_1\tau_M}{\tau_1\left(1 - \frac{1}{\Omega_M}\right) - \tau_M}\right)\ln\left(\frac{\tau_1\left(1 - \frac{1}{\Omega_M}\right)}{\tau_M}\right), \quad (27C)$$

where "ln" represents the logarithm to the base e, the natural logarithm.

For $\phi_2$, an analysis almost identical to equations 20 through 27 above is derived. The differences are two-fold. First, a biphasic waveform reverses the flow of current through the myocardium during $\phi_2$. Reversing the flow of current in the circuit model changes the sign on the current. The sign changes on the right hand side of equation 23.

The second difference is the step taken to incorporate an independent $\phi_2$ into the charge burping model. Therefore, the $\phi_2$ ODE incorporates the $C_2$ capacitor set and their associated leading-edge voltage, $V_2$, for the $\phi_2$ portion of the pulse. Then $\tau_2$ represents the $\phi_2$ time constant; $\tau_2 = RC_2$, and $V_S = -V_2 e^{-t/\tau_2}$. Equation 23 now becomes:

$$\frac{dV_M}{dt} + \left(\frac{V_M}{\tau_M}\right)\left(1 - \frac{1}{\Omega_M}\right) = \frac{-V_2 e^{-t/\tau_2}}{\tau_M \Omega_S}. \quad (29)$$

Equation 29 is again a first-order linear ODE. In a similar manner, its general solution is determined to be:

$$V_{M2}(t) = ke^{(-t/\tau_M)\left(1 - \frac{1}{\Omega_M}\right)} - \left(\frac{V_2}{\Omega_M}\right)\left(\frac{\tau_2}{\tau_2\left(1 - \frac{1}{\Omega_M}\right) - \tau_M}\right). \quad (30)$$

To determine the constant of integration k, the value of $V_{M2}$ at the end of $\phi_1$ is $$V_{M2}(0) = V_{M1}(d_{\phi1}) = V_{\phi1}, \quad (31)$$

where $d_{\phi1}$ is the overall time of discharge for $\phi_1$ and $V_1$ is the voltage left on the cell at the end of $\phi_1$. Applying the initial condition to equation 30 and solving for k:

$$k = V_{\phi1} + \left(\frac{V_2}{\Omega_S}\right)\left(\frac{\tau_2}{\tau_2\left(1 - \frac{1}{\Omega_M}\right) - \tau_M}\right) \quad (32)$$

The solution to the initial-value problem for $\phi_2$ is $$V_{M2}(t) = \left(\frac{V_2}{\Omega_S}\right)\left(\frac{\tau_2}{\tau_2\left(1 - \frac{1}{\Omega_M}\right) - \tau}\right)\left(e^{-t(\tau_M)\left(1 - \frac{1}{\Omega_M}\right)} - e^{-t/\tau_2}\right) + \quad (33)$$

$$V_{\phi1}e^{-(t/\tau_M)\left(1 - \frac{1}{\Omega_M}\right)}.$$

Equation 33 provides a means to calculate the residual membrane potential at the end of $\phi_2$ for the cells that were not stimulated by $\phi_1$. Setting Equation 33 equal to zero, we solve for t, there by determining the duration of $\phi_2$, denoted $d\phi_2$, such that $V_{M2}(d\phi_2) = 0$. By designing $\phi_2$ with a duration $d\phi_2$, the biphasic shock pulse removes the residual charge placed on a cell by $\phi_1$. We determine $d\phi_2$ to be:

$$d_{\phi2} = \left(\frac{\tau_2\tau_M}{\tau_2\left(1 - \frac{1}{\Omega_M}\right) - \tau_M}\right)\cdot\ln\left[1 + \left(\frac{\tau_2\left(1 - \frac{1}{\Omega_M}\right) - \tau_M}{\tau_2}\right)\left(\frac{\Omega_S V_{\phi1}}{V_2}\right)\right]. \quad (34)$$

From the equations above an optimal monophasic or biphasic defibrillation waveform may be calculated for an external defibrillator.

As an example, an external defibrillator may be designed as set forth below. Assume a monophasic truncated exponential shock pulse, a 200 μF capacitor, so that $\tau_1 = R \cdot (200 \mu F)$. Suppose also that the external defibrillator is designed to apply the maximal cardiac cell response design rule (equation 27C) to determine the duration of the discharge. Suppose further that the human cardiac cell time constant is estimated to be 3±1 ms. Further assume that the external defibrillator energy source comprises five 1000 μF capacitors in series to implement a 200 μF capacitor bank. If each capacitor is charged to 400V, for a total of 2000V for the leading-edge voltage, this represents 400 J of stored energy. The transchest elements are estimated at: 82% current through the thoracic cage; 14% through the chest wall and lungs in parallel; and 4% of applied current through the lung in series with the heart. Then the membrane resistance coefficient $\Omega_M = 5.9$, and the system resistance coefficient $\Omega_S = 2.3$ Then the table below illustrates the application of the design rule as the t resistance ranges from 25 Ω to 200 Ω:

| R (Ω) | $\tau_1$ | d ($\phi_1$) | $V_{final}$ | $E_{delivered}$ |
| --- | --- | --- | --- | --- |
| 25 | 5.2 | 5.05 | 757 | 343 |
| 50 | 10.2 | 6.90 | 1017 | 297 |
| 75 | 15.2 | 8.15 | 1170 | 263 |
| 100 | 20.2 | 9.10 | 1275 | 238 |
| 125 | 25.2 | 9.90 | 1350 | 216 |
| 150 | 30.2 | 10.55 | 1410 | 201 |
| 175 | 35.2 | 11.15 | 1457 | 186 |
| 200 | 40.2 | 11.65 | 1497 | 176 |

Description of Present Invention

As stated above, the present invention provides a method and apparatus for delivering a truncated damped sinusoidal waveform. Having developed the transthoracic model above, a general description of the method and apparatus of the present invention will now be given.

Figure 6:
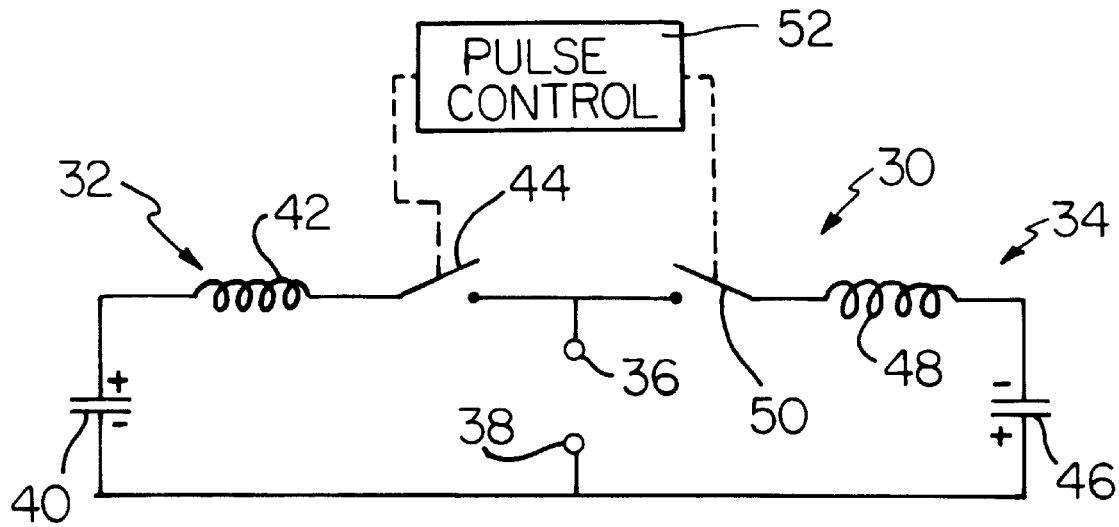
FIG. 6 is a simplified schematic illustration of an external defibrillation sinusoidal pulse generating circuit.

FIG. 6 is a simplified schematic illustration of a general external defibrillation pulse generation circuit 30 which is configured for producing truncated damped sinusoidal biphasic (i.e., multiphasic) and/or monophasic defibrillation pulses (without the external modeling parameters of FIGS.

4 and 5). As shown, circuit 30 includes a first pulse component generation circuit 32 and a second pulse component generation circuit 34 which are connected in a parallel arrangement to a pair of electrode terminals 36 and 38. First pulse component generation circuit 32 includes a charge storage device such as capacitor 40, an inductor 42 and a circuit or device represented by switch 44 connected to one another in a series arrangement between terminals 36 and 38. Similarly, second pulse component generation circuit 34 includes a capacitor 46, an inductor 48 and a switch 50 connected to one another in a series arrangement between terminals 36 and 38. Switches 44 and 50 are coupled to and are independently controlled by a pulse controller 52 to initiate and terminate (truncate) defibrillation pulses.

Figure 2A:
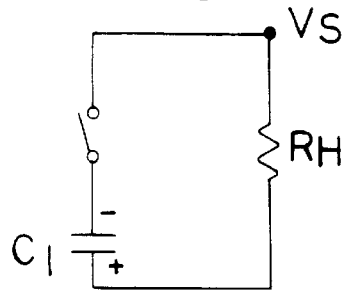
FIG. 2a is a very simplified defibrillator model.
Figure 2B:
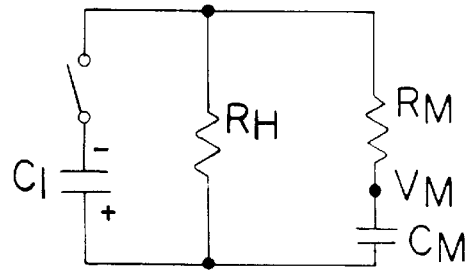
FIG. 2b is a known monophasic defibrillation model.
Figure 3:
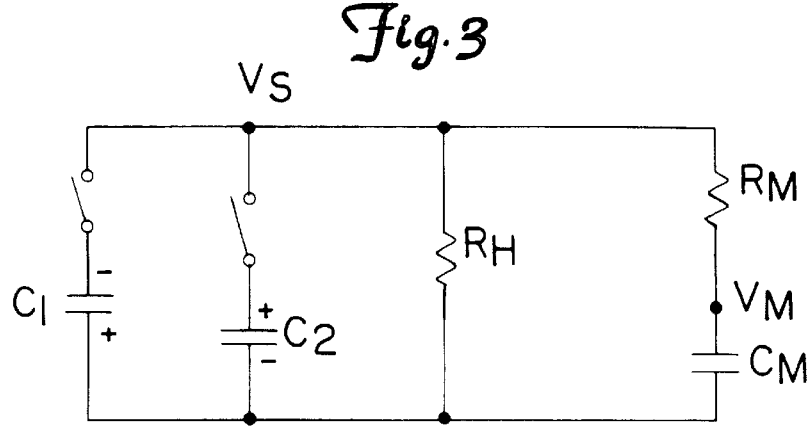
FIG. 3 is a known biphasic defibrillation model.

The defibrillation pulses generated by circuit 30 will be applied to the torso of a patient in a conventional manner through a pair of electrodes, such as electrodes 24 from FIG. 2, electrically connected to terminals 36 and 38. In the preferred embodiment of the present invention, capacitors 40 and 46 are in the range of 25 $\mu F$–500 $\mu F$, and inductors 42 and 48 are in the range of 25 mH–500 mH. Estimated optimal values for capacitors 40 and 46 and inductors 42 and 48 are chosen for AED 10. In one embodiment, capacitor 40 is chosen to be 45 $\mu F$, capacitor 46 is chosen to be 180 $\mu F$, inductor 42 is chosen to be 250 mH and inductor 48 is chosen to be 250 mH.

Figure 7:
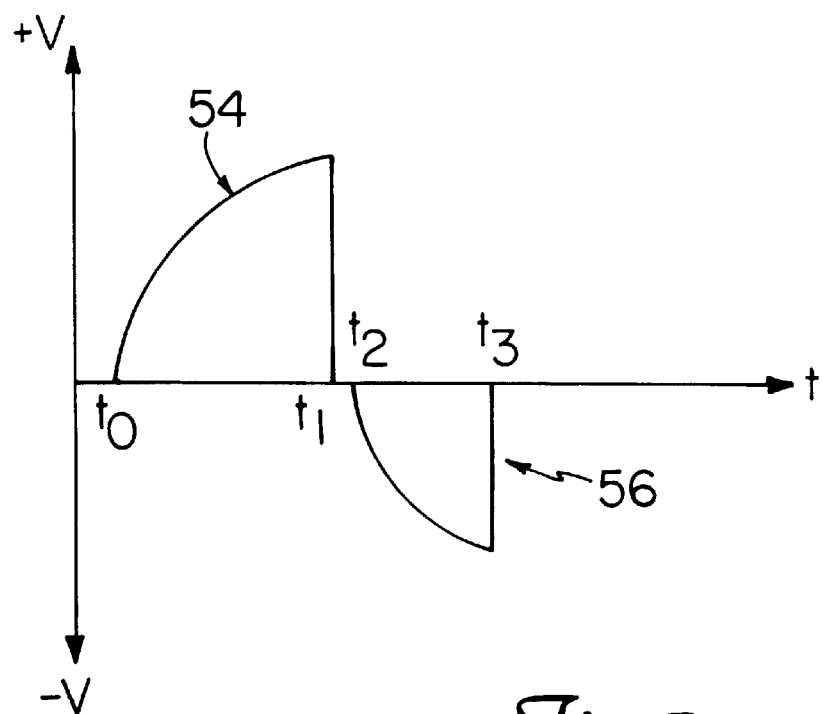
FIG. 7 is an illustration of a truncated damped sinusoidal biphasic defibrillation pulse.

FIG. 7 is an illustration of a truncated damped sinusoidal biphasic defibrillation pulse which includes a first phase having a positive polarity component 54 and a second phase having a negative polarity pulse component 56. With capacitors 40 and 46 charged to their respective opposite polarity charge potentials, pulse controller 52 causes the circuit element(s) forming switch 44 to switch to a closed state at time $t_0$ to initiate first phase pulse component 54. At time $t_1$ switch 44 is switched to an open state to terminate pulse component 54. Although not shown in FIG. 7, pulse component 54 can also be truncated by circuitry controlled by pulse controller 52 which rapidly discharges capacitor 40 and inductor 42. Second phase pulse component 56 is initiated by pulse controller 52 at time $t_2$ by switching switch 50 to a closed state. At time $t_3$ switch 50 is switched to an open state to truncate second phase pulse component 56.

Figure 8A:
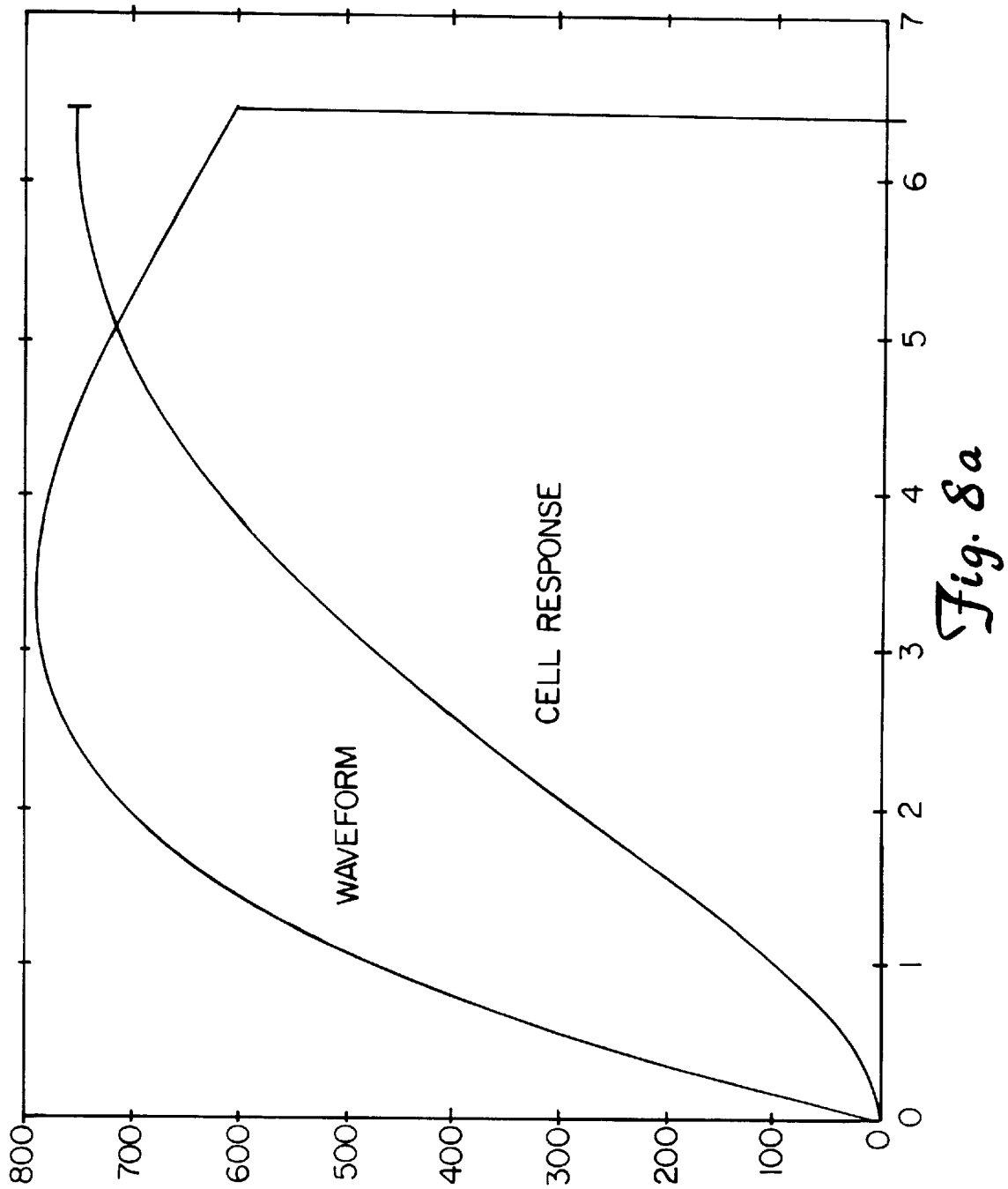
FIGS. 8a, 8b and 8c are illustrations of damped sinusoidal waveforms and associated cell membrane responses.

It has been determined that one preferred and efficacious waveform has first phase component 54 with a relatively slow onset with respect to a convention damped sinusoidal pulse. In particular, the shape of first phase pulse component 54 can be tailored in an attempt to match the cell membrane response to the first pulse component. These preferred characteristics of first phase component 54 are illustrated generally in FIGS. 8a, 8b and 8c. FIGS. 8a illustrates a damped sinusoidal pulse waveform and the associated cell membrane response. This diagram assumes an 80 Ω load for the heart, capacitor 40 is 45 $\mu F$ and inductor 42 is 250 mH.

Figure 8B:
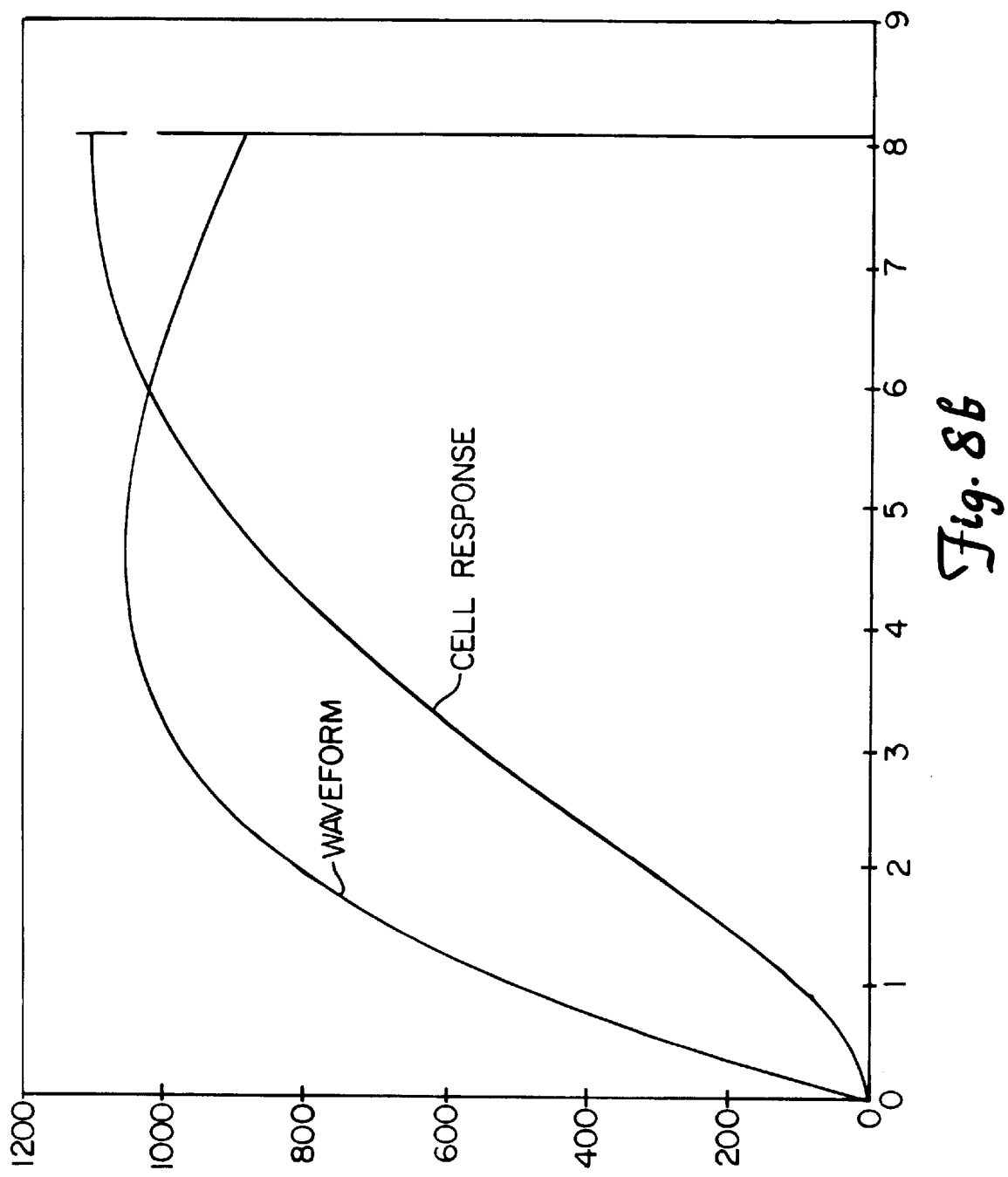

The damped sinusoidal pulse waveform shown in FIG. 8b has a slower onset than that of the waveform shown in FIG. 8a, with little or no loss in the onset time of the associated cell membrane response. In this embodiment, an 80 Ω load is again assumed for the heart, capacitor 40 is 90 $\mu F$ and inductor 42 is 250 mH. The damped sinusoidal pulse waveform shown in FIG. 8c has an even slower onset time than that of the waveform shown in FIG. 8b, and again generates an associated cell membrane response with little or no loss in the onset time with respect to the cell membrane response generated by the waveform shown in FIG. 8a. In this embodiment, an 80 Ω load is again assumed, capacitor 40 is 180 $\mu F$ and inductor 42 is again 250 mH.

Figure 8C:
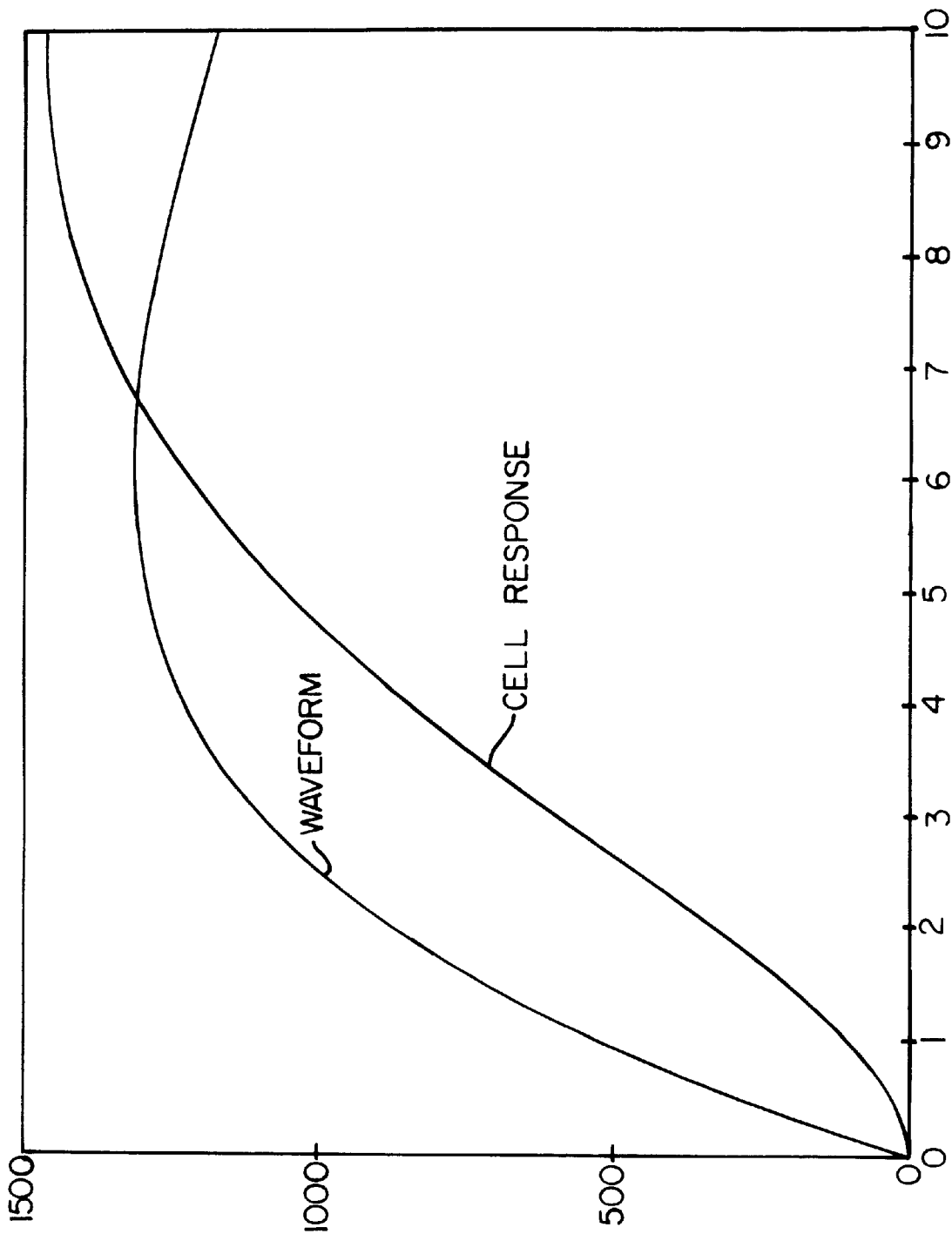

Another preferred and effacious waveform has first phase component 54 which is truncated at a time which closely corresponds to the time that the maximum or peak cell membrane response is achieved (i.e., when the slope of the cell membrane response is zero). First phase components 54 having these characteristics are also illustrated in FIGS. 8a, 8b and 8c. Defibrillation efficacy can thereby be maximized with respect to the peak cell response design rule using relatively low energy and short waveforms.

The ability of circuit 30 to independently generate and shape second phase pulse component 56 also contributes to the efficacy of the waveform. In particular, this characteristic of the circuit enables second phase pulse component 56 to be tailored in voltage, length, shape and other characteristics to maximize its charge burping effects on the cell membrane. For example, second phase component 56 can have a duration which is different than the duration of first phase component 54, and which is truncated at the time that the cell membrane response reaches about zero.

In operation the present invention develops and applies a truncated damped sine wave to a patient that approximates the patient's cell response and that truncates at the peak cell response. In order to develop a waveform that matches (or attempts to match) the cell response, it is first necessary to measure a patient dependent parameter, such as impedance, voltage, current, charge or other measurable parameters of the patient. The values of capacitors 40 and 46, and inductors 42 and 48 are preselected, thus once the patient dependent parameter is determined a first duration of a monophasic or $\phi_1$ of a biphasic waveform can be determined using the equations developed above for modeling a human chest. In particular, solving for t in equation 36 below yields the optimal duration $d_1$ for a monophasic or $\phi_1$ of a biphasic waveform. Equation 39 below is used to determine the optimal duration for $\phi_2$ of the biphasic waveform. As can be appreciated from the above, the determination of the optimal duration of $\phi_2$ is independent from that of $\phi_1$.

After the optimal durations have been determined, capacitor 40 is charged. For biphasic waveforms, capacitor 42 is then charged. Switch 44 is then closed discharging capacitor 40 to electrical terminals 36 and 38. At the end of the optimally calculated duration $d_1$ switch 44 is opened to truncate the phase one waveform. Switch 50 is then closed discharging capacitor 42 to electrode terminals 36 and 38. At the end of the optimally calculated duration $d_2$ switch 50 is opened to truncate the $\phi_2$ portion of the biphasic waveform.

The design rules for the truncated damped sine waveform are now developed. Equation 19 is now used to solve for $V_M$ by replacing $V_S$ with the defibrillation circuit model for a damped sine waveform, as shown in equation 14B. Doing so provides:

$$\frac{dV_M}{dt} + \frac{V_M}{\tau_M}\left(1 - \frac{1}{\Omega_M}\right) = \left(\frac{V_1}{\tau_M \Omega_S}\right)\left(\frac{\tau_{C1}}{\tau_{C1} - \tau_{L1}}\right)\left(e^{\frac{-t}{\tau_{C1}}} - e^{\frac{-t}{\tau_{L1}}}\right). \quad (35)$$

The solution of equation 35 for $V_M$ is found in the same manner as described above for equations 24–27, so that:

$$V_{M1}(t) = \qquad (36)$$
$$L_{11}\cdot\left(e^{-\left(\frac{t}{\tau_{C1}}\right)} - e^{-\left(\frac{t}{\tau_M}\right)\left(1-\frac{1}{\Omega_M}\right)}\right) - L_{12}\cdot\left(e^{-\left(\frac{t}{\tau_{L1}}\right)} - e^{-\left(\frac{t}{\tau_M}\right)\left(1-\frac{1}{\Omega_M}\right)}\right)$$

where $$L_{11} = \left(\frac{V_1}{\Omega_S}\right)\left(\frac{\tau_{C1}}{\tau_{C1}-\tau_{L1}}\right)\left(\frac{\tau_{C1}}{\tau_{C1}\left(1-\frac{1}{\Omega_M}\right)-\tau_M}\right) \quad (37)$$

and

-continued $$L_{12} = \left(\frac{V_1}{\Omega_S}\right)\left(\frac{\tau_{C1}}{\tau_{C1} - \tau_{L1}}\right)\left(\frac{\tau_{L1}}{\tau_{L1}\left(1 - \frac{1}{\Omega_M}\right) - \tau_M}\right). \quad (38)$$

Figure 9:
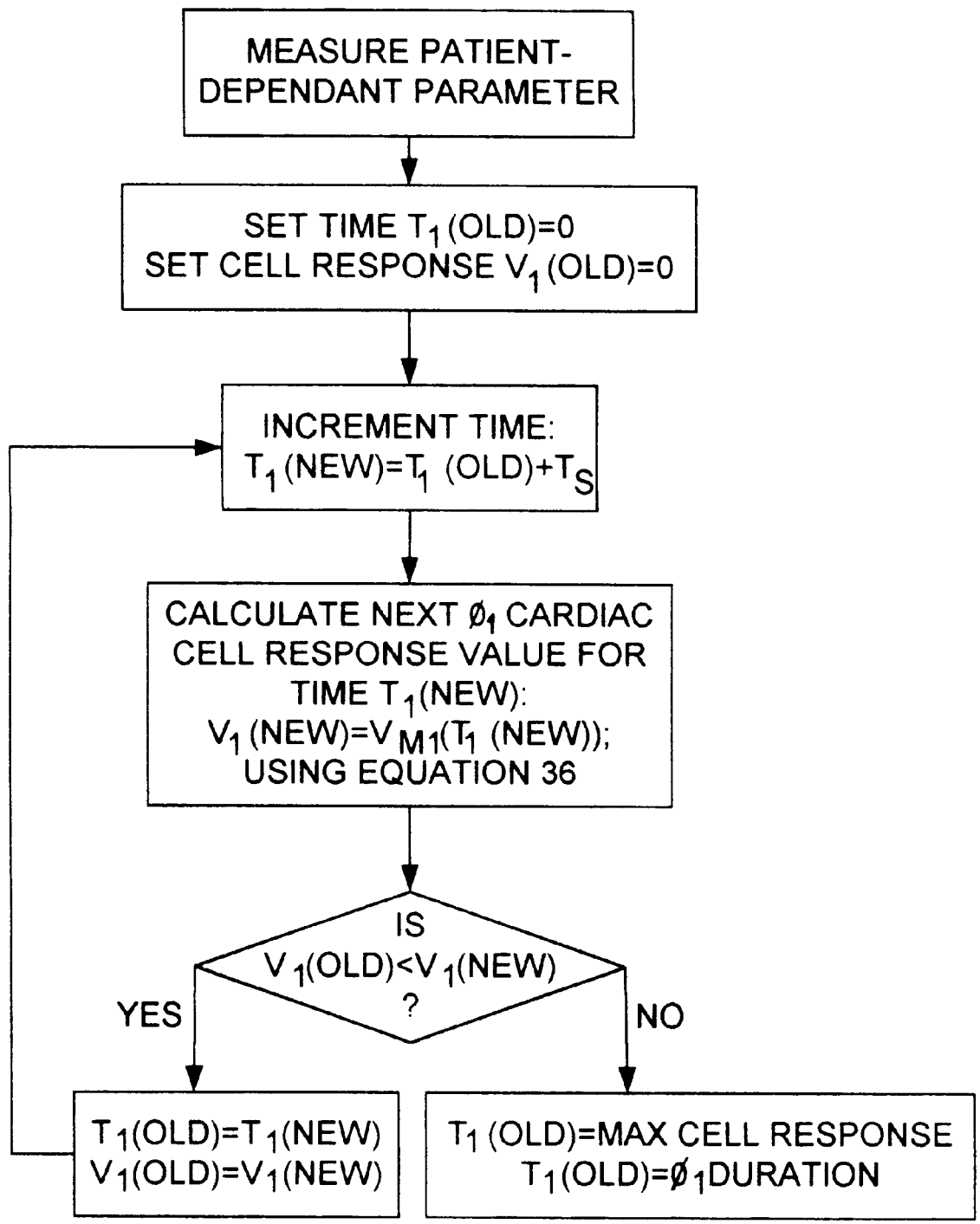
FIG. 9 illustrates a flow chart for the determination and use of the truncation time for $\phi_1$ of a damped sine wave shock pulse.

To maximize cell response, $V_{M1}(t)$ is differentiated, the derivative $(dV_{M1}(t)/dt)$ is to zero, and the time t is determined such that $(dV_{M1}(t)/dt)=0$. The time t solution of the differential equation of $V_{M1}(t)$ provides the design rule for the duration of $\phi_1$ of the truncated damped sine waveform. For a predetermined time step $T_S$ (for example 50 ms) a real-time implementation of the truncation process is described in FIG. 9 for $\phi_1$ of the damped sine wave shock pulse. The time $T_1(\text{old})$ determined from this process is the time of maximum cell response and therefore the duration of $\phi_1$.

Figure 10:
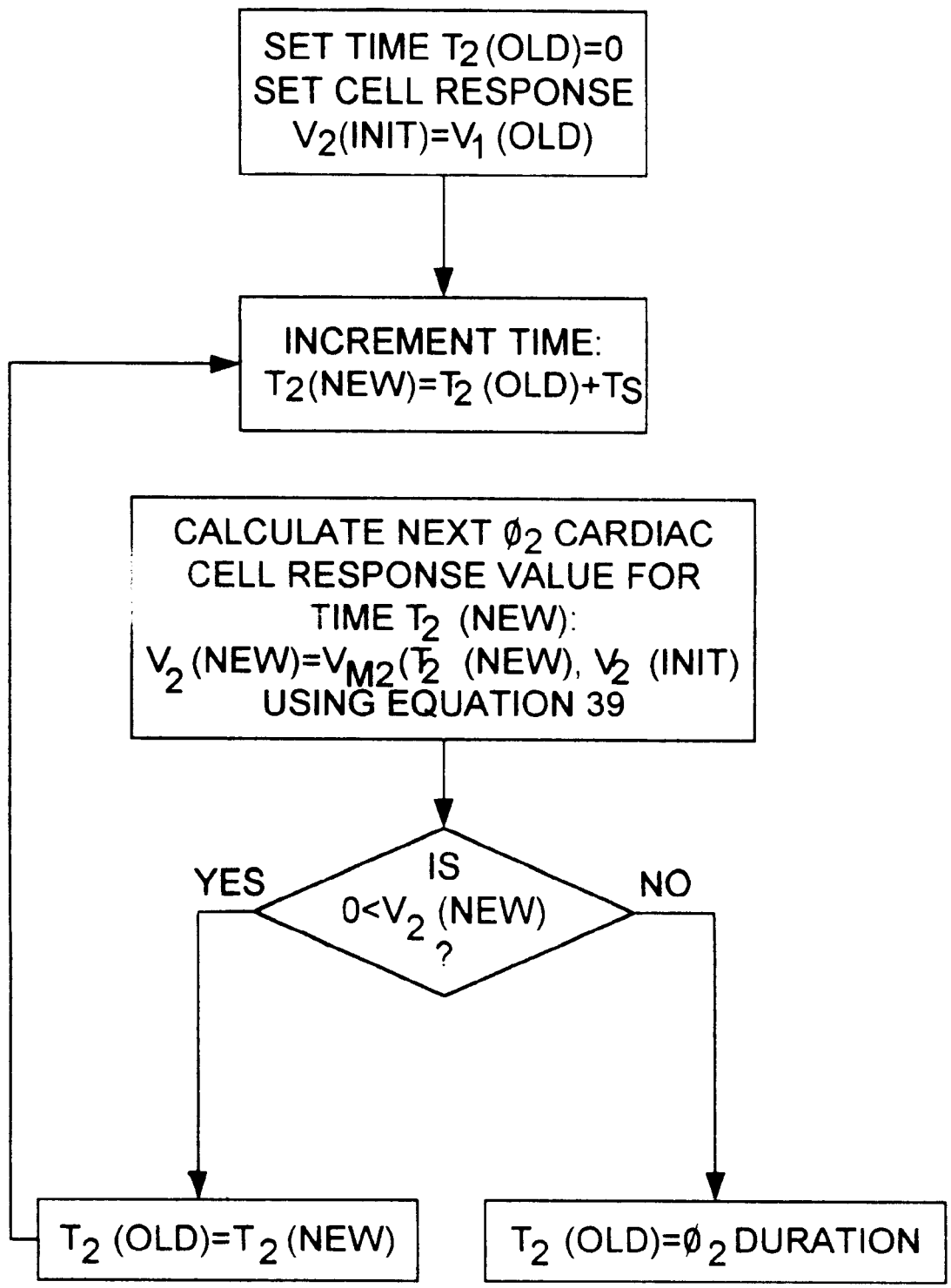
FIG. 10 illustrates a flow chart for the determination and use of the truncation time for $\phi_2$ of the damped sine wave shock pulse.

In the same manner that equation 33 is derived, the cardiac cell response to $\phi_2$ of a damped sine wave shock pulse is found to be $$V_{M2}(t) = L_{21}\left(e^{-\left(\frac{t}{\tau_{L2}}\right)} - e^{-\left(\frac{t}{\tau_M}\right)\left(1-\frac{1}{\Omega_M}\right)}\right) - L_{22}\left(e^{-\left(\frac{t}{\tau_{C2}}\right)} - e^{-\left(\frac{t}{\tau_M}\right)\left(1-\frac{1}{\Omega_M}\right)}\right) + \left[V_{\phi1} e^{-\left(\frac{t}{\tau_M}\right)\left(1-\frac{1}{\Omega_M}\right)}\right] \quad (39)$$

in accordance with FIG. 5b; where $$L_{21} = \left(\frac{V_2}{\Omega_S}\right)\left(\frac{\tau_{C2}}{\tau_{C2} - \tau_{L2}}\right)\left(\frac{\tau_{L2}}{\tau_{L2}\left(1 - \frac{1}{\Omega_M}\right) - \tau_M}\right) \quad (40)$$

and $$L_{22} = \left(\frac{V_2}{\Omega_2}\right)\left(\frac{\tau_{C2}}{\tau_{C2} - \tau_{L2}}\right)\left(\frac{\tau_{C2}}{\tau_{C2}\left(1 - \frac{1}{\Omega_M}\right) - \tau_M}\right) \quad (41)$$

and $$V\phi_1 = V_{M1}(d_1)$$

where $d_1$ is the duration for $\phi_1$ of the damped sine wave shock pulse. To determine the $\phi_2$ design rule, equation 39 is set to zero and the time t is determined such that $V_{M2}(t)=0$. A real-time implementation of $\phi_2$ truncation process is described in FIG. 10.

The present invention applies a waveform that defibrillates the heart based on models of cell response, and which truncates a monophasic waveform or $\phi_1$ of a biphasic waveform at the peak or approximate peak cell response time. As desired, the present invention further applies a second phase of a waveform that further defibrillates the heart based on models of the cell response, and which truncates $\phi_2$ of a biphasic waveform at the time a cell response is reset to the cell's natural resting state.

It should be noted and understood that $\phi_2$ is independent from $\phi_1$. In order to design an effective $\phi_2$ waveform, the only thing needed from $\phi_1$ is to know where the cell response was left when $\phi_1$ truncated. Phase 1 may be designed based on the truncated damped sine wave equations given above, while $\phi_2$ may be designed and implemented utilizing other technology such as single capacitor discharge technology, and vice-versa. The corresponding design rules for a $\phi_1$ circuitry may be used in conjunction with the design rules for a $\phi_2$ circuitry, regardless of the specific circuitry used to implement each phase of a monophasic or biphasic shock pulse.

Although the present invention has been described with reference to preferred embodiments, workers skilled in the art will recognize that changes may be made in form and detail without departing from the spirit or scope of the present invention.

What is claimed:

1. An external defibrillator for delivering a truncated damped sinusoidal waveform comprising:
   a first charge storage component;
   a first inductive component connected in series with the first charge storage component;
   a first truncating switch connected in series with the first charge storage component and the first inductive component;
   a second charge storage component;
   a second inductive component connected in series with the second charge storage component;
   a second truncating switch connected in series with the second charge storage component and the second inductive component; and
   a pair of electrode connectors connected across the circuits formed by the first charge storage component, the first inductive component, and the first switch and the second charge storage component, the second inductive component, and the second switch, wherein the waveform control circuitry is connected to the first truncating switch and the second truncating switch and independently operates the first and second truncating switches.

2. The defibrillator of claim 1, further comprising electrodes for connection to the electrode connectors, wherein the electrodes are adapted to be placed on the exterior of a patient for delivering the waveform to the patient's heart through the patient's chest wall.

3. The defibrillator of claim 1, wherein the second inductor component comprises an inductor having an inductance value within the range of 25 mH to 500 mH.

4. The defibrillator of claim 1, wherein the second charge storage component comprises a capacitor having a capacitance value within the range of 25 µF to 500 µF.

5. A method of applying a damped sinusoidal waveform to a pair of electrodes of an external defibrillator having a first capacitive component, a first inductive component, a first truncating switch, and waveform control circuitry, the method including the steps of:
   a) monitoring a first patient-dependent parameter;
   b) determining a first discharge duration based on the first monitored patient-dependent parameter;
   c) charging the first capacitive component;
   d) closing the first truncating switch to discharge the first capacitive component through the first inductive component to the electrodes; and
   e) opening the first truncating switch to truncate the discharge of the first capacitive component to the electrodes at the expiration of the determined first discharge duration.

6. The method of claim 5 wherein the first patient-dependent parameter is impedance.

7. The method of claim 5 wherein the first patient-dependent parameter is current.

8. The method of claim 5 wherein the first patient-dependent parameter is voltage.

9. The method of claim 5 wherein the first patient-dependent parameter is charge.

10. The method of claim 5, wherein step b) is carried out using a quantitative model of a patient including at least one of a chest component, a heart component and a cardiac cell component.

11. The method of claim 5 wherein the step of determining the first discharge duration includes using a predetermined design rule.

12. The method of claim 11 wherein the predetermined design rule is based on a transthoracic model that represents the time course of cardiac cell membrane potential during a transthoracic shock pulse.

13. The method of claim 5 wherein the step of determining the first discharge duration includes determining a truncation point of the waveform based on a maximum cardiac cell membrane response.

14. The method of claim 13 wherein determining the truncation point further comprises:

iteratively calculating a voltage value of a cardiac cell response function at incrementally increasing time values of a first discharge duration function until the voltage value of the cardiac cell response function reaches a maximum, at which time the waveform is truncated and a maximum time value of the first discharge duration function equals the first discharge duration.

15. The method of claim 14 wherein determining the truncation point further comprises the steps of:

f) setting a prior time value of a first discharge duration function equal to zero and setting a prior voltage value of a cardiac cell response function equal to zero;

g) determining a subsequent time value of the first discharge duration function by adding an incremental time period $T_S$ to the prior time value of the first discharge duration function;

h) determining a subsequent voltage value of the cardiac cell response function at the subsequent time value;

i) comparing the subsequent voltage value to the prior voltage value and upon the subsequent voltage value being greater than the prior voltage value, resetting the prior voltage value equal to the subsequent voltage value and resetting prior time value equal to the subsequent time value; and j) repeating steps g)–i) until the subsequent voltage value of the cardiac cell response function is no greater than the prior voltage value of the cardiac cell response function at which time the truncation point is established wherein the subsequent time value equals the first discharge duration and the subsequent voltage value represents the maximum cardiac cell membrane response.

16. The method of claim 14 the cardiac cell response function further comprises calculating the following equation:

$$V_{M1}(t) = L_{11} \cdot \left(e^{-\left(\frac{t}{\tau_{C1}}\right)} - e^{-\left(\frac{t}{\tau_M}\right)\left(1-\frac{1}{\Omega_M}\right)}\right) - L_{12} \cdot \left(e^{-\left(\frac{t}{\tau_{L1}}\right)} - e^{-\left(\frac{t}{\tau_M}\right)\left(1-\frac{1}{\Omega_M}\right)}\right)$$

where $\tau_{C1}$=RC1, and $\tau_M$=$R_M C_M$, where $R_M$ represents a cardiac cell membrane resistive component and $C_M$ represents a cardiac cell membrane capacitance component, $\Omega_M$ represents a cardiac cell membrane impedance, and $\tau_{L1}$=L1/R, where L1 represents an inductive component of a defibrillation circuit model, C1 represents a capacitive component of the defibrillation circuit model, and R represents at least a body impedance, where $$L_{11} = \left(\frac{V_1}{\Omega_S}\right)\left(\frac{\tau_{C1}}{\tau_{C1}-\tau_{L1}}\right)\left(\frac{\tau_{C1}}{\tau_{C1}\left(1-\frac{1}{\Omega_M}\right)-\tau_M}\right)$$

where $\Omega_S$ represents a system impedance, and $$L_{12} = \left(\frac{V_1}{\Omega_S}\right)\left(\frac{\tau_{C1}}{\tau_{C1}-\tau_{L1}}\right)\left(\frac{\tau_{L1}}{\tau_{L1}\left(1-\frac{1}{\Omega_M}\right)-\tau_M}\right).$$

where $V_1$ represents a voltage on a charged capacitor C1.

17. The method of claim 16 wherein R equals $R_S$+$R_B$, where $R_S$ represents a system impedance and $R_B$ represents the body impedance.

18. The method of claim 17 wherein the calculating step further comprises determining the system impedance including at least one of a defibrillation circuit model impedance and an electrode impedance.

19. The method of claim 17 wherein the calculating step further comprises determining the body impedance including at least one of a thoracic cage impedance, a chest wall impedance, a lung series impedance, a lung parallel impedance, and a heart impedance.

20. The method of claim 5, wherein the defibrillator further includes a second capacitive component, a second inductive component and a second truncating switch, the method further including the steps of:

f) determining a second discharge duration based on a second monitored patient-dependent parameter;

g) charging the second capacitive component;

h) closing the second truncating switch to discharge the second capacitive component to the electrodes; and i) opening the second truncating switch to truncate the discharge of the second capacitive component to the electrodes at the expiration of the determined second discharge duration.

21. The method of claim 20 wherein the second patient-dependent parameter is charge.

22. The method of claim 20 wherein the second patient-dependent parameter is voltage.

23. The method of claim 20 wherein the second patient-dependent parameter is impedance.

24. The method of claim 20 wherein the second patient-dependent parameter is current.

25. The method of claim 20 wherein the second patient-dependent parameter is independent of the first patient-dependent parameter.

26. The method of claim 20, wherein step f) is carried out independently of step b).

27. The method of claim 20, wherein step f) is carried out using a quantitative model of a patient including at least one of a chest component, a heart component and a cardiac cell membrane component.

28. The method of claim 20 wherein step f) further comprises:

determining a truncation point based on a residual cardiac cell membrane potential.

29. The method of claim 28 wherein the determining the truncation point further comprises:

a) iteratively calculating a voltage value of the cardiac cell response function at incrementally increasing time values of a second discharge duration function until the voltage value of the cardiac cell response function reaches a minimum, at which time the waveform is truncated and a maximum time value of the second discharge duration function represents the second discharge duration.

30. The method of claim 29 wherein the step of iterative calculation further comprises the steps of:
   j) setting a prior value of a second discharge duration function equal to zero and setting a prior voltage value of a cardiac cell response function equal to the voltage value of the cardiac cell response function at the end of the first discharge duration;
   k) determining a subsequent time value of the second discharge duration function by adding an incremental time period $T_S$ to the prior time value of the second discharge duration function;
   l) determining a subsequent voltage value of the cardiac cell response function based on the subsequent time value and on the voltage value of the cardiac cell response function at the end of the first discharge duration;
   m) comparing the subsequent voltage value to the prior voltage value and upon the subsequent voltage value being greater than the prior voltage value, resetting the prior time value equal to the subsequent time value; and
   n) repeating steps k)–m) until the subsequent voltage value of the cell response function is equal to zero at which time the truncation point is established, wherein the subsequent time value equals the second discharge duration and identifies the expiration of the waveform.

31. The method of claim 29 the cardiac cell response function further comprises calculating the following equation:

$$V_{M2}(t) = L_{21}\left(e^{-\left(\frac{t}{\tau_{L2}}\right)} - e^{-\left(\frac{t}{\tau_M}\right)\left(1-\frac{1}{\Omega_M}\right)}\right) - L_{22}\left(e^{-\left(\frac{t}{\tau_{C2}}\right)} - e^{-\left(\frac{t}{\tau_M}\right)\left(1-\frac{1}{\Omega_M}\right)}\right) + \left[V_{\phi 1} e^{-\left(\frac{t}{\tau_M}\right)\left(1-\frac{1}{\Omega_M}\right)}\right]$$

where $\tau_{C2} = RC2$
$\tau_M = R_M C_M$, where $R_M$ represents a cardiac cell membrane resistive component and
$C_M$ represents a cardiac cell membrane capacitance component,
$\Omega_M$ represents a cardiac cell membrane impedance,
$\tau_{L2} = L2/R$,
L2 represents an inductive component of a defibrillation circuit model,
C2 represents a capacitive component of the defibrillation circuit model, and
R represents at least a body impedance, $$L_{21} = \left(\frac{V_2}{\Omega_S}\right)\left(\frac{\tau_{C2}}{\tau_{C2}-\tau_{L2}}\right)\left(\frac{\tau_{L2}}{\tau_{L2}\left(1-\frac{1}{\Omega_M}\right)-\tau_M}\right)$$

and $$L_{22} = \left(\frac{V_2}{\Omega_2}\right)\left(\frac{\tau_{C2}}{\tau_{C2}-\tau_{L2}}\right)\left(\frac{\tau_{C2}}{\tau_{C2}\left(1-\frac{1}{\Omega_M}\right)-\tau_M}\right)$$

and
$V\phi_1 = V_{M1}(d_1)$ where $d_1$ is the duration for $\phi_1$ of the damped sine wave shock pulse, and where $V_{M1}(d1)$ represents the first discharge maximum cardiac cell response function.

32. The method of claim 31 wherein R equals $R_S+R_B$, where $R_S$ represents a system impedance including at least one of a defibrillation circuit model impedance and an electrode impedance, and $R_B$ represents the body impedance including at least one of a thoracic cage impedance, a chest wall impedance, a lung series impedance, a lung parallel impedance, and a heart impedance.

33. A method of applying a monophasic damped sinusoidal waveform to a pair of electrodes of an external defibrillator having a pulse generation circuit, including a capacitive component and an inductive component, connected to the pair of electrodes, and having waveform control circuitry for selectively activating the pulse generation circuit, the method including the steps of:
   a) monitoring a patient-dependent parameter;
   b) determining a discharge duration of the waveform based on the monitored patient-dependent parameter;
   c) activating the pulse generation circuit with the waveform control circuitry to selectively discharge the waveform through the electrodes; and
   d) deactivating the first pulse generation circuit at the expiration of the discharge duration.

34. The method of claim 33 wherein step c) further comprises: charging the capacitive component of the pulse generation circuit prior to selectively discharging the waveform.

35. The method of claim 33 wherein step b) further comprises:
   a) iteratively calculating a voltage value of a cardiac cell response function at incrementally increasing time values of a discharge duration function until the voltage value of the cardiac cell response function reaches a maximum, at which time the waveform is truncated and a maximum time value of the discharge duration function represents the discharge duration.

36. A method of applying a biphasic damped sinusoidal waveform, having a first phase and a second phase, to a pair of electrodes of an external defibrillator having a first pulse generation circuit and a second pulse generation circuit connected in parallel to the pair of electrodes, and having waveform control circuitry for selectively activating at least one of the first and second pulse generation component circuits, the method including the steps of:
   a) monitoring a patient-dependent parameter;
   b) determining a first discharge duration based on a first monitored patient-dependent parameter;
   c) activating the first pulse generation circuit with the waveform control circuitry to selectively discharge the first phase of the waveform through the electrodes;
   d) deactivating the first pulse generation circuit at the expiration of the first discharge duration;
   e) determining a second discharge duration based on a second monitored patient-dependent parameter;
   f) activating the second pulse generation circuit with the waveform control circuitry to selectively discharge the second phase of the waveform through the electrodes, the second phase having a polarity opposite a polarity of the first phase; and
   g) deactivating the second pulse generation circuit at the expiration of the second discharge duration.

37. The method of claim 36 wherein the first discharge duration of step b) is based on a first predetermined design rule and the second discharge duration step of step e) is based on a second predetermined design rule independent of the first predetermined design rule.

38. The method of claim 37 wherein the first predetermined design rule includes using a maximum cardiac cell response.

39. The method of claim 37 wherein the second predetermined design rule includes using a minimum residual cardiac cell membrane potential.

40. The method of claim 36 wherein the first patient-dependent parameter is independent of the second patient-dependent parameter.

41. A method of truncating a transchest external defibrillation shock pulse at the expiration of a discharge duration wherein the pulse, when applied through electrodes positioned on a patient's torso, will terminate upon reaching a maximum response in the patient's cardiac cell membranes, the method including the steps of:

a) providing a cardiac cell response function based on a quantitative cardiac cell membrane model;

b) setting a prior time value of a discharge duration function equal to zero and setting a prior voltage value of the cardiac cell response function equal to zero;

c) determining a subsequent time value of the discharge duration function by adding a predetermined incremental time period $T_S$ to the prior time value of the discharge duration function;

d) determining a subsequent voltage value of the cardiac cell response function at the subsequent time value;

e) comparing the subsequent voltage value to the prior voltage value and upon the subsequent voltage value being greater than the prior voltage value, resetting the prior voltage value equal to the subsequent voltage value and resetting the prior time value equal to the subsequent time value; and f) repeating steps c)–e) until the subsequent voltage value of the cardiac cell response function is no greater than the prior voltage value of the cardiac cell response function at which time the shock pulse is truncated, wherein the subsequent voltage value represents a maximum voltage value of the cardiac cell response function and the subsequent time value is the discharge duration.

42. A method of determining a truncation point of a transchest external defibrillation shock pulse, wherein the pulse, when applied through electrodes positioned on a patient's torso, will terminate upon a response in the patient's cardiac cell membranes reaching a minimum potential, the method including the steps of:

a) setting a prior time value of a truncation point function equal to zero and setting a prior voltage value of a cardiac cell response function equal to an initial voltage value of the patient's cardiac cell membranes;

b) determining a subsequent time value of the truncation point function by adding a predetermined incremental time period $T_S$ to the prior time value of the truncation point function;

c) determining a subsequent voltage value of the cardiac cell response function based on the subsequent time value and on the initial voltage of the patient's cardiac cell membranes;

d) comparing the subsequent voltage value to the prior voltage value and upon the subsequent voltage value being greater than the prior voltage value, resetting the prior time value equal to the subsequent time value; and e) repeating steps b)–d) until the subsequent voltage value of the cardiac cell response function is equal to zero at which time the truncation point is established at the subsequent time value of the truncation point function wherein the subsequent time value represents a discharge duration of the shock pulse.

43. The method of claim 42 wherein step a) further comprises the cardiac cell response function being dependent on a quantitative cardiac cell membrane model.

44. A method of truncating a transchest external defibrillation shock pulse at the expiration of a discharge duration, wherein the pulse, when applied through electrodes positioned on a patient's torso, will terminate upon reaching a maximum response in the patient's cardiac cell membranes, the method including the steps of:

a) iteratively calculating a voltage value of a cardiac cell response function at incrementally increasing time values of a discharge duration function until the voltage value of the cardiac cell response function reaches a maximum, at which time the shock pulse is truncated and a maximum time value of the discharge duration function represents the discharge duration.

45. The method of claim 44 wherein the time values of the discharge duration function are separated by a predetermined time interval $T_S$ and an initial time value of the discharge duration function is equal to zero.

46. A method of truncating a transchest external defibrillation shock pulse at the expiration of a discharge duration wherein, the pulse, when applied through electrodes positioned on a patient's torso will terminate upon elimination of a residual electrical potential on the patient's cardiac cell membranes, the method including the steps of:

a) iteratively calculating a voltage value of a cardiac cell response function at incrementally increasing time values of a discharge duration function until the voltage value of the cardiac cell response function reaches a minimum, at which time the shock pulse is truncated and a maximum time value of the discharge duration function equals the discharge duration.

47. The method of claim 46 wherein the time values of the discharge duration function are separated by a predetermined time interval $T_S$ and an initial time value of the discharge duration function is equal to zero.

48. The method of claim 46 and further comprising initiating the calculating step with an initial voltage value of the cardiac cell response function having an absolute value greater than zero.

49. The method of claim 48 wherein the initial voltage value equals a maximum cardiac cell response occurring in a previously applied external defibrillation shock pulse.

50. An external defibrillator for delivering a truncated damped sinusoidal waveform comprising:

a first charge storage component;

a first inductive component connected in series with the first charge storage component wherein the first inductive component comprises an inductor having an inductance value within the range of 25 mH to 500 mH; and a first truncating switch connected in series with the first charge storage component and the first inductive component; and waveform control circuitry connected to the first truncating switch for independently operating the first truncating switch.

51. An external defibrillator for delivering a truncated damped sinusoidal waveform comprising:

a first charge storage component wherein the first charge storage component comprises a capacitor having a capacitance value within the range of 25 $\mu$F to 500 $\mu$F;

a first inductive component connected in series with the first charge storage component; and a first truncating switch connected in series with the first charge storage component and the first inductive component; and waveform control circuitry connected to the first truncating switch for independently operating the first truncating switch.

52. A method of applying a monophasic damped sinusoidal waveform to a pair of electrodes of an external defibrillator having a pulse generation circuit connected to the pair of electrodes, and having waveform control circuitry for selectively activating the pulse generation circuit, the method including the steps of:

a) monitoring a patient-dependent parameter;

b) determining a discharge duration of the waveform based on the monitored patient-dependent parameter by iteratively calculating a voltage value of a cardiac cell response function at incrementally increasing time values of a discharge duration function until the voltage value of the cardiac cell response function reaches a maximum, at which time the time value of the discharge duration function represents the determined discharge duration;

c) activating the pulse generation circuit with the waveform control circuitry to selectively discharge the waveform through the electrodes; and d) deactivating the first pulse generation circuit at the expiration of the determined discharge duration.

* * * * *